(12) United States Patent
Meyer-Almes et al.

(10) Patent No.: US 11,801,251 B2
(45) Date of Patent: Oct. 31, 2023

(54) SELECTIVE HDAC8 INHIBITORS AND THEIR USES

(71) Applicant: HOCHSCHULE DARMSTADT, Darmstadt (DE)

(72) Inventors: Franz-Josef Meyer-Almes, Otzberg-Lengfeld (DE); Christian Meyners, Darmstadt (DE); Alexander Kleinschek, Darmstadt (DE); Patricia Haus, Laudenbach (DE)

(73) Assignee: HOCHSCHULE DARMSTADT, Darmstadt (DE)

(*) Notice: Subject to any disclaimer, the term of this patent is extended or adjusted under 35 U.S.C. 154(b) by 183 days.

(21) Appl. No.: 17/141,520

(22) Filed: Jan. 5, 2021

(65) Prior Publication Data
US 2021/0220370 A1    Jul. 22, 2021

Related U.S. Application Data

(62) Division of application No. 15/771,550, filed as application No. PCT/EP2016/076615 on Nov. 3, 2016, now abandoned.

(30) Foreign Application Priority Data

Nov. 3, 2015    (DE) .......................... 102015118842.2

(51) Int. Cl.
| | | |
|---|---|---|
| A61K 31/542 | (2006.01) | |
| C07D 513/04 | (2006.01) | |
| A61P 35/00 | (2006.01) | |
| A61K 45/06 | (2006.01) | |

(52) U.S. Cl.
CPC ............ *A61K 31/542* (2013.01); *A61K 45/06* (2013.01); *A61P 35/00* (2018.01); *C07D 513/04* (2013.01); *Y02A 50/30* (2018.01)

(58) Field of Classification Search
CPC ...... A61K 31/542; C07D 513/04; A61P 35/00
See application file for complete search history.

(56) References Cited

U.S. PATENT DOCUMENTS

2009/0076019 A1    3/2009    Tyers et al.

FOREIGN PATENT DOCUMENTS

| DE | 2811131 A1 | 9/1979 |
| WO | 2012153768 A1 | 11/2012 |
| WO | 2014040087 A1 | 3/2014 |
| WO | 2014160947 A1 | 10/2014 |
| WO | 2016056606 A1 | 4/2016 |

OTHER PUBLICATIONS

Chakrabarti et al. Trends in Pharmacological Sciences 2015, 36 (7), 481-492.*
Rettig et al. Cell Death and Disease 2015, 6, e1657, pp. 1-13.*
Asami, Y. et al., "A simple set-and-mix assay for screening of protein kinase inhibitors in cell lysates." Analytical Biochemistry, 2011, 418: 44-49.
Ghebremariam, Y. T. et al., "A Novel and Potent Inhibitor of Dimethylarginine Dimethylaminohydrolase: A Modulator of Cardiovascular Nitric Oxide." J. Pharmacol. Exp. Ther., Jan. 2014, 348: 69-76.
Kleinschek, Alexander et al., "Potent and Selective Non-hydroxamate Histone Deacetylase 8 Inhibitors." Chemmedchem, vol. 11, Nov. 2016, p. 2598-2606.
Mizuhara, Tsukasa et al., "Concise synthesis and anti-HIV activity of pyrimido[1,2-c][1,3]benzothiazin-6-imines and related tricyclic heterocycles." Organic & Biomolecular Chemistry, Royal Society of Chemistry, vol. 10:(33), Sep. 2012, p. 6792-6802.
Mizuhara, Tsukasa et al., "Efficient Synthesis of Pyrimido[1,2-c][1,3]benzothiazin-6-imines and Related Tricyclic Heterocycles by SNAr-Type C—S, C—N, or C—O Bond Formation with Heterocumulenes." J. Org. Chem., vol. 75, 2010, p. 265-268.
Okazaki, Shiho et al., "Investigations of possible prodrug structures for 2-(2-mercaptophenyl)tetrahydropyrimidines: reductive conversion from anti-HIV agents with pyrimidobenzothiazine and isothiazolopyrimidine scaffolds." Org Biomol Chem, vol. 13, Mar. 2015, p. 4706-4713.
Ried, Walter et al., "2-(4,5-Dihydro-1H-imidazol-2-yl)thiophenol und analoge Verbindungen als Bausteine in der Heterocyclensynthese." Liebigs Ann Chem, 1988, p. 599-601.
Giannini, Giuseppe et al., "Hydroxamic acid based histone deacetylase inhibitors with confirmed activity against the malaria parasite", Bioorganic & Medicinal Chemistry Letters, 2014, vol. 25, pp. 459-461.
Stolfa, Diana A et al., "Molecular Basis for the Antiparasitic Activity of a Mercaptoacetamide Derivative That Inhibits Histone Deacetylase 8 (HDAC8) from the Human Pathogen Schistosoma mansoni", J. Mol. Biol., 2014, vol. 426, pp. 3442-3453.
Mizuhara et al., J. Org. Chem. 2010, 75, 265-268.
Mizuhara et al., Org. Biomol. Chem. 2012, 10, 6792-6802.
Okazaki et al., Org. Biomol. Chem. 2015, 13, 4706-4713.
Okazaki et al., Bioorg. Med. Chem. 2015, 23, 1447-1452.

* cited by examiner

*Primary Examiner* — Irina Neagu
(74) *Attorney, Agent, or Firm* — SALIWANCHIK, LLOYD & EISENSCHENK

(57) ABSTRACT

The present invention relates to small molecule compounds based on benzopyrimido- or benzoimidazo-thiazin-imine as well as their (synthesis) intermediates and their use as HDAC inhibitors, in particular HDAC8 inhibitors. The present invention also relates to the use of said compounds in the treatment of cancer and as therapeutic agents for eukaryotic parasites and respective methods of treatment.

20 Claims, 14 Drawing Sheets

PCI-34051

Vorinostat (SAHA)

Panobinostat (Farydak®)

6a (also named 13b)

6b (also named 13c)

7c (also named 13d)

7b (also named 13e)

7d (also named 13f)

7e (also named 13g)

7f (also named 13h)

▼ HDAC1
● HDAC5
■ HDAC7
◆ HDAC8

P2742 = 13a
KA188 = 13l
KA192 = Thion, n=2, R4=CH3

SELECTIVE HDAC8 INHIBITORS AND THEIR USES

CROSS REFERENCE TO RELATED APPLICATIONS

This application is a Divisional Application of application No. Ser. No. 15/771,550, filed Apr. 27, 2018; which is a National Stage Application of International Application Number PCT/EP2016/076615, filed Nov. 3, 2016; which claims priority to German Patent Application No. 10 2015 118 842.2, filed Nov. 3, 2015.

FIELD OF THE INVENTION

The present invention relates to small molecule compounds based on benzopyrimido- or benzoimidazo-thiazin-imine as well as their (synthesis) intermediates and their use as HDAC inhibitors, in particular HDAC8 inhibitors. The present invention also relates to the use of said compounds in the treatment of cancer and as therapeutic agents for eukaryotic parasites and respective methods of treatment.

BACKGROUND OF THE INVENTION

Today, cancer is still one of the most threatening diseases in common societies. 13% of the worldwide deaths (7.9 million people) in 2007 were caused by cancer. As the second most common cause of death (USA), exceeded only by heart diseases, cancer remains a burden to the health and even the funds off many societies (see e.g. Cancer Facts & FIGS. 2009). The start of a cancer disease can be caused by environmental influences or the incorporation of toxins into a healthy cell, leading to several damages in its DNA. Cancer cells are characterized by their out-of-control growth, their invasion into different tissues and the extensive spreading over the whole body through bloodstream and lymph system migration.

Conventionally, cancer is treated by a mixture of chemotherapy, surgery and radiation, depending on the individual type of cancer. For a long time DNA crosslinking agents like cisplatin were applied in treatments with chemotherapy to induce apoptosis.

During the last decades of cancer research several new targets were explored, leading to new approaches for cancer treatments. Among these targets, the enzyme class of the so called histone deacetylases (HDACs) is one of the most promising ones.

In the nucleus of cells, the DNA is structurally tensely packed by forming nucleosomes, which comprise of multiple units of a protein octamer and attached convoluted DNA. Those proteins, called histones, have a strong influence on the accessibility for transcriptional proteins by binding the DNA over acetylated histone-lysine residues. Acetylated lysine residues form tense structures with the negatively charged backbone of the DNA leading to reduced gene expression.

HDACs play a great role in controlling the acetylation state of lysine residues located at the ends of histones. Occurring as a natural substrate, acetylated lysines become deacetylated by HDACs resulting in reduced gene expression due to a less accessible DNA structure. The loss of acetylations can be restored by the antagonistic histone acetyl-transferases (HATs).

In consequence of their fundamental influence on regulating gene expression, HDACs are associated with several diseases and vice versa are valid targets for cancer treatments (Bieliauskas and Pflum, 2008).

In humans, the overall family of HDAC proteins contains 18 different members separated into four classes by their homology to yeast proteins, cellular localization and the structure of their active sites. Class I comprises of HDAC-1, -2, -3 and -8 which are homologue to the yeast protein RPD3 and retain mostly located in the nucleus. Class II HDAC members are divided into the further subclasses IIa and IIb. Class IIa Includes HDAC-4, -5, -7 and -9 which are homologue to yeast HDA1-deacetylase and contain one active site. In contrast, the HDAC IIb members HDAC-6 and -10 contain two active sites. However HDAC-10 carries only one completely functional active site while the second C-terminally localized domain lacks important residues of the active site. Class IIa members have the possibility of shuttling between cytoplasm and the nucleus. In contrast HDAC IIb members are localized in the cytoplasm. The Class IV member HDAC-11 shares a similar catalytic domain with Class I and II members. Yet, no substrate could be identified for this protein. All Class I, II and IV members are zinc-dependent deacetylases. In contrast Class III proteins are $NAD^+$ dependent and denoted as Sirtuins due to their yeast homologue SirT2 (Finnin et al., 1999; Schrump 2009; Marks and Xu, 2009).

Despite their strong structural similarities, HDACs are involved in different non-redundant processes, which are tissue specific. Knock-out of HDAC-1, -2, -3 or -7 in mice are lethal in early embryonic states due to aberrant angiogenesis or cell cycle control. Mice with knock-out for HDAC-4, -5, -6, or -9 are viable with occurring abnormalities in cardiovascular, bone and muscle development. In cancer tissue a single knock-down of one HDAC results in specific symptoms. For example, HDAC-2 knock-down in colon cancer cells induces growth arrest, while lagging this effect in osteosarcoma or breast-cancer. Conducted studies found high expression levels of class I HDACs in many primary human cancer cell lines (breast, pancreas, lung, esophageal, gastric, colon, ovary and thyroid). Yet, less is known about expression levels of class II HDACs in cancer cell lines (Schrump 2009; Nakagawa et al., 2007).

The high expression values of different HDAC members in cancer cell lines and their strong influence on gene regulation led to a new approach for cancer treatments based on histone deacetylase inhibitors (HDACi's). In the last few years several types of HDACi's could be identified for the zinc-dependent HDAC classes (I, II and IV). Four main classes are established till today: hydroxamates, cyclic peptides, small fatty acids and benzamidines.

Off these four, the hydroxamates are the most enlightened group until today. In general, their structure consists of a variable cap group and a metal-binding hydroxamic acid group. Both parts are connected through an aliphatic linker. This schedule is basically in accordance to the natural substrate which complexes the zinc in the active site with an acetyl group instead of the hydroxamic acid. One of the first potent hydroxamate HDACi's was isolated from *Streptomyces* bydroscopicus: Trichostation A (TSA) (Kim et al., 2000). Based on this structure, a second very potent HDACi was synthesized: Vorinostat (SAHA) (Butler et al., 2000). SAHA was one of the first HDACi that passed all clinical trials and was applied for treatment of cutaneous T-cell lymphoma (CTCL).

Several studies clearly identified HDAC8 to be involved in various cancer diseases like T-cell lymphoma (Balasubramanian et al., 2008; U.S. Pat. No. 8,906,954), neuroblastoma (Oehme et al., 2009), urothelial cancer (Niegisch et al., 2013) and breast cancer (Park et al., 2011) as well as in neural crest development (Haberland et al., 2009).

However, most of the very potent HDACi's, in particular TSA, SAHA, Panobinostat, are rather unselective inhibitors. The inhibition of several or nearly all HDACs goes along with several site effects (see also WO 2007/019116 A1). To avoid these pharmacological issues research for HDAC isoform specific inhibitors became an urgent challenge.

There is a need in the art for improved HDAC inhibitors, in particular for HDAC inhibitors with improved selectivity.

BRIEF SUMMARY OF THE INVENTION

According to the present invention this object is solved by using a compound having general formula I or II

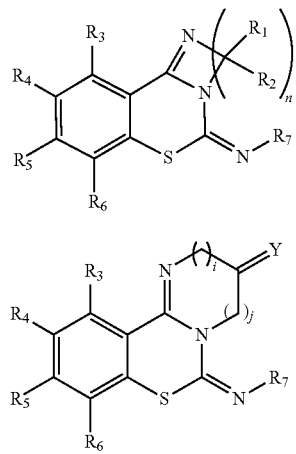

wherein
n is an integer of 1 to 7, preferably 1 to 4,
i, j are each an integer of 1 to 5, preferably 1 to 3,
Y is O, $NR_{11}$ and S,
$R_1$, $R_2$, $R_3$, $R_4$, $R_5$, $R_6$ and $R_7$ are each independently selected from hydrogen; halogen, such as I, Cl, Br, F, $NO_2$, CN, $SO_3$, $N(R_{10})_2$, O—X, S—X, $NR_8$—X, —$NR_{10}C(=O)$—X, $S(=O)$—X, $S(=O)_2$—X, $NHS(=O)_2$—X, $C_1$-$C_6$ alkyl-X, $C_2$-$C_6$ alkenyl-X, $C_2$-$C_6$ alkynyl-X, $C_1$-$C_6$ heteroalkyl-X, $C_1$-$C_6$ fluoroalkyl-X, partially fluorinated $C_1$-$C_6$ alkyl-X, $C_1$-$C_6$ alkyl-O—X, $C_1$-$C_3$ alkyl-O—$C_1$-$C_3$ alkyl-X, $C_1$-$C_6$ alkyl-$NR_8$—X, $C_1$-$C_3$ alkyl-$NR_8$—$C_1$-$C_3$ alkyl-X, $C_1$-$C_6$ alkyl-$C(=O)NR_8$—X, $C_1$-$C_3$ alkyl-$C(=O)$ NR—$C_1$-$C_3$ alkyl-X, $C_1$-$C_6$ alkyl-$NR_8C(=O)$—X, $C_1$-$C_3$ alkyl-$NR_8C(=O)$—$C_1$-$C_3$ alkyl-X, $C_1$-$C_6$ alkyl-S—X, $C_1$-$C_3$ alkyl-S—$C_1$-$C_3$ alkyl-X, $C_1$-$C_6$ alkyl-$S(=O)$—X, $C_1$-$C_3$ alkyl-$S(=O)$—$C_1$-$C_3$ alkyl-X, $C_1$-$C_6$ alkyl-$S(=O)_2$—X, $C_1$-$C_3$ alkyl-$S(=O)_2$—$C_1$-$C_3$ alkyl-X, $C(=O)$—X, $C(=O)$—$NR_8$—X, $C(=O)$—$C_1$-$C_6$ alkyl-X, substituted or unsubstituted $C_2$-$C_{10}$ heterocycloalkyl, substituted or unsubstituted aryl, heteroaryl, $Si_1$—$Si_3$ silyl-X, $Si_2$—$Si_4$ siloxane-X;

X is hydrogen, or a substituted or unsubstituted group selected from aryl, heteroaryl, $C_1$-$C_6$ alkyl, $C_2$-$C_6$ alkenyl, $C_1$-$C_6$ fluoroalkyl, partially fluorinated $C_1$-$C_6$ alkyl, $C_1$-$C_3$ alkylamino$C_1$-$C_3$ alkoxy, hydroxy$C_1$-$C_3$ alkylamino$C_1$-$C_3$ alkoxy, $C_2$-$C_8$ heterocycloalkyl$C_1$-$C_3$ alkoxy, $C_2$-$C_8$ heterocycloalkyl$C_1$-$C_2$ alkyl, CN, $NO_2$, $SO_3$, $CO_2R_9$, $C(=O)R_9$, S—$R_9$, $S(=O)$—$R_9$, $S(=O)_2$—$R_9$, $NR_{10}C(=O)$—$R_9$, $C(=O)N(R_{10})_2$, $S(=O)_2N(R_{10})_2$, $NR_{10}S(=O)_2$—$R_9$, $OC(=O)N(R_{10})_2$, $NR_{10}C(=O)O$—$R_9$, —$OC(=O)O$—$R_9$, $NHC(=O)NH$—$R_9$, $OC(=O)R_9$, $N(R_{10})_2$, $C_1$-$C_2$ alkylN$(R_{10})_2$, $C_2$-$C_6$ alkyne, $C_1$-$C_6$ heteroalkyl, $C_3$-$C_2$cycloalkyl, $C_2$-$C_{10}$ heterocycloalkyl, $Si_1$—$Si_3$ silyl, $Si_2$—$Si_4$ siloxane;

$R_8$ is selected from hydrogen, $C_1$-$C_6$ alkyl, phenyl or benzyl;

$R_9$ is a substituted or unsubstituted group selected from $C_1$-$C_6$ alkyl, $C_1$-$C_6$ fluoroalkyl, partially fluorinated $C_1$-$C_6$ alkyl, $C_3$-$C_8$ cycloalkyl, $C_2$-$C_8$ heterocycloalkyl, aryl, and heteroaryl;

$R_{10}$ and $R_{11}$ are each independently selected from hydrogen, or a substituted or unsubstituted group selected from $C_1$-$C_6$ alkyl, $C_1$-$C_6$ fluoroalkyl, partially fluorinated $C_1$-$C_6$ alkyl, $C_1$-$C_6$ heteroalkyl, $C_3$-$C_8$ cycloalkyl, $C_2$-$C_8$ heterocycloalkyl, aryl, and heteroaryl;

or a pharmaceutically accepted salt or pharmaceutically acceptable prodrug thereof, as inhibitor of enzymes of the histone deacetylase (HDAC) family.

According to the present invention this object is solved by using a compound having general formula III or IV

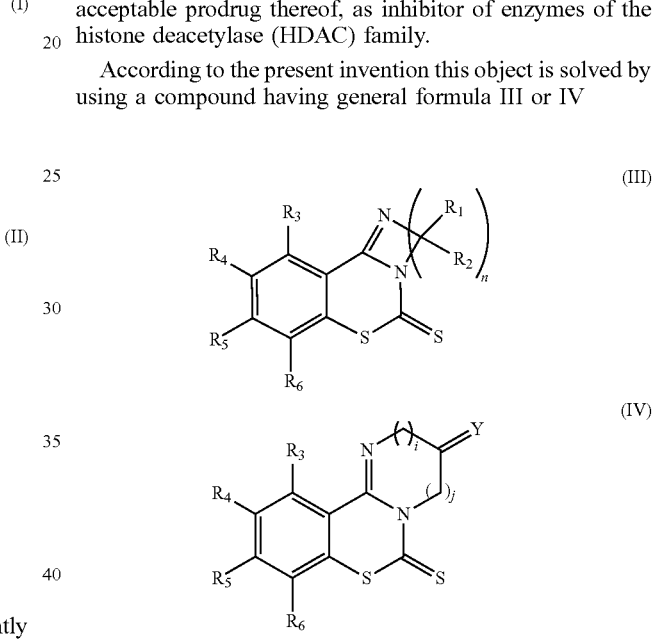

wherein
n is an integer of 1 to 7, preferably 1 to 4,
i, j are each an integer of 1 to 5, preferably 1 to 3,
Y is O, $NR_{11}$ and S,
$R_1$, $R_2$, $R_3$, $R_4$, $R_5$, $R_6$ and $R_7$ are each independently selected from hydrogen,
halogen, such as I, Cl, Br, F,
$NO_2$, CN, $SO_3$, $N(R_{10})_2$,
O—X, S—X, $NR_8$—X, —$NR_{10}C(=O)$—X, $S(=O)$—X, $S(=O)_2$—X, $NHS(=O)_2$—X,
$C_1$-$C_6$ alkyl-X, $C_2$-$C_6$ alkenyl-X, $C_2$-$C_6$ alkynyl-X, $C_1$-$C_6$ heteroalkyl-X, $C_1$-$C_6$ fluoroalkyl-X, partially fluorinated $C_1$-$C_6$ alkyl-X, $C_1$-$C_6$ alkyl-O—X, $C_1$-$C_3$ alkyl-O—$C_1$-$C_3$ alkyl-X, $C_1$-$C_6$ alkyl-$NR_8$—X, $C_1$-$C_3$ alkyl-$NR_8$—$C_1$-$C_3$ alkyl-X, $C_1$-$C_6$ alkyl-$C(=O)NR_8$—X, $C_1$-$C_3$ alkyl-$C(=O)$ $NR_8$—$C_1$-$C_3$ alkyl-X, $C_1$-$C_6$ alkyl-$NR_8C(=O)$—X, $C_1$-$C_3$ alkyl-$NR_8C(=O)$—$C_1$-$C_3$ alkyl-X, $C_1$-$C_6$ alkyl-S—X, $C_1$-$C_3$ alkyl-S—$C_1$-$C_3$ alkyl-X, $C_1$-$C_6$ alkyl-$S(=O)$—X, $C_1$-$C_3$ alkyl-$S(=O)$—$C_1$-$C_3$ alkyl-X, $C_1$-$C_6$ alkyl-$S(=O)_2$—X, $C_1$-$C_3$ alkyl-$S(=O)_2$—$C_1$-$C_3$ alkyl-X, $C(=O)$—X, $C(=O)$—$NR_8$—X, $C(=O)$—$C_1$-$C_6$ alkyl-X, substituted or unsubstituted $C_2$-$C_{10}$ heterocycloalkyl, substituted or unsubstituted aryl, heteroaryl, $Si_1$—$Si_3$ silyl-X, $Si_2$—$Si_4$ siloxane-X;

X is hydrogen, or a substituted or unsubstituted group selected from aryl, heteroaryl, $C_1$-$C_6$ alkyl, $C_2$-$C_6$ alkenyl, $C_1$-$C_6$ fluoroalkyl, partially fluorinated $C_1$-$C_6$ alkyl, $C_1$-$C_3$ alkylamino$C_1$-$C_3$ alkoxy, hydroxy$C_1$-$C_3$ alkylamino$C_1$-$C_3$ alkoxy, $C_2$-$C_8$ heterocycloalkyl$C_1$-$C_3$ alkoxy, $C_2$-$C_8$ heterocycloalkyl$C_1$-$C_2$ alkyl, CN, $NO_2$, $SO_3$, $CO_2R_9$, C(=O)$R_9$, S—$R_9$, S(=O)—$R_9$, S(=O)$_2$—$R_9$, $NR_{10}$C(=O)—$R_9$, C(=O)N($R_{10}$)$_2$, S(=O)$_2$N($R_{10}$)$_2$, $NR_{10}$S(=O)$_2$—$R_9$, OC(=O)N($R_{10}$)$_2$, $NR_{10}$C(=O)O—$R_9$, —OC(=O)O—$R_9$, NHC(=O)NH—$R_9$, OC(=O)$R_9$, N($R_{10}$)$_2$, $C_1$-$C_2$ alkylN($R_{10}$)$_2$, $C_2$-$C_6$ alkyne, $C_1$-$C_6$ heteroalkyl, $C_3$-$C_{10}$cycloalkyl, $C_2$-$C_{10}$ heterocycloalkyl, $Si_1$—$Si_3$ silyl, $Si_2$—$Si_4$ siloxane;

$R_8$ is selected from hydrogen, $C_1$-$C_6$ alkyl, phenyl or benzyl;

$R_9$ is a substituted or unsubstituted group selected from $C_1$-$C_6$ alkyl, $C_1$-$C_6$ fluoroalkyl, partially fluorinated $C_1$-$C_6$ alkyl, $C_3$-$C_8$ cycloalkyl, $C_2$-$C_8$ heterocycloalkyl, aryl, and heteroaryl;

$R_{10}$ and $R_{11}$ are each independently selected from hydrogen, or a substituted or unsubstituted group selected from $C_1$-$C_6$ alkyl, $C_1$-$C_6$ fluoroalkyl, partially fluorinated $C_1$-$C_6$ alkyl, $C_1$-$C_6$ heteroalkyl, $C_3$-$C_8$ cycloalkyl, $C_2$-$C_8$ heterocycloalkyl, aryl, and heteroaryl; or a pharmaceutically accepted salt or pharmaceutically acceptable prodrug thereof, as inhibitor of enzymes of the histone deacetylase (HDAC) family.

According to the present invention this object is solved by a pharmaceutical composition comprising
 (a) at least one compound according to the present invention,
 (b) optionally, pharmaceutically acceptable excipient(s) and/or carrier.

According to the present invention this object is solved by a compound according to the invention or pharmaceutical composition of the present invention for use in the treatment of cancer.

According to the present invention this object is solved by a compound according to the invention or pharmaceutical composition of the present invention for use as therapeutic agent against eukaryotic parasites.

According to the present invention this object is solved by a compound according to the invention or pharmaceutical composition of the present invention for use in the treatment of infections with eukaryotic parasites.

According to the present invention this object is solved by a method of treatment of cancer, comprising the step of administering to a subject a therapeutically effective amount of a compound according to the invention or a pharmaceutical composition according to the invention.

According to the present invention this object is solved by a method of an infection with eukaryotic parasites, comprising the step of
 administering to a subject a therapeutically effective amount of a compound according to the invention or a pharmaceutical composition according to the invention.

DESCRIPTION OF THE PREFERRED EMBODIMENTS OF THE INVENTION

Figure 1A:
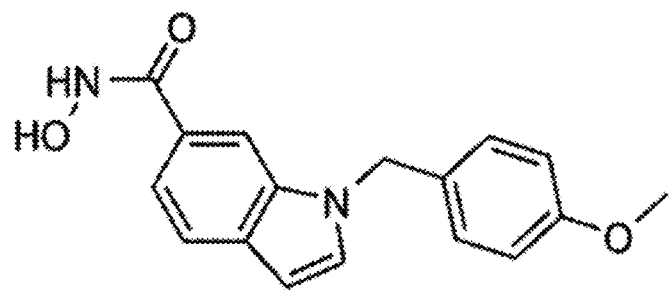
FIG. 1A-1B—Structure of HDAC inhibitors. (1A) Shown are the structures of the prior art HDAC inhibitors PCI-34051, Vorinostat (SAHA), and Panobinostat (Farydak®). (1B) Shown are structures of novel HDAC inhibitors of the invention having general formula I or II.
Figure 1A:
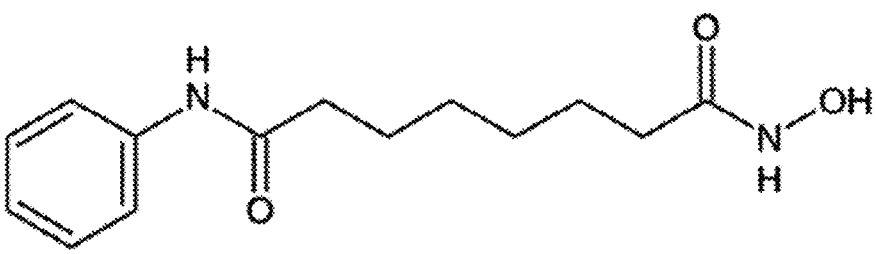
Figure 1A:
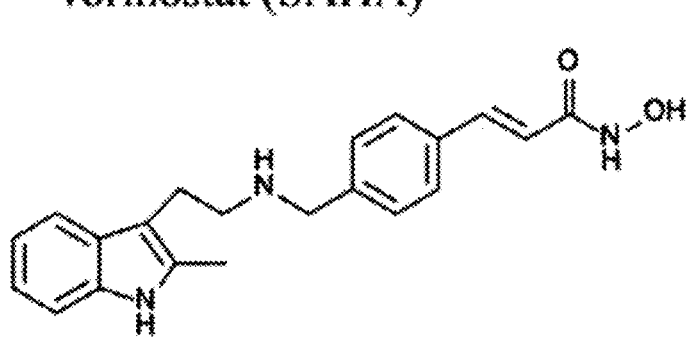
Figure 1B:
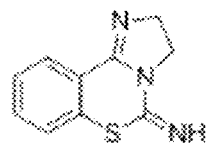
Figure 1B:
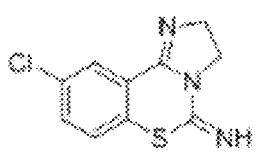
Figure 1B:
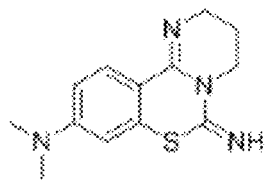
Figure 1B:
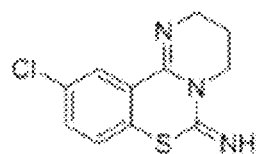
Figure 1B:
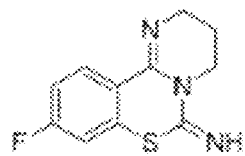
Figure 1B:
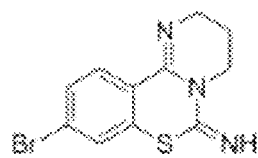
Figure 1B:
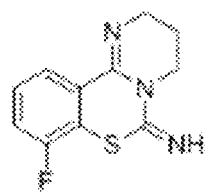
Figure 2A:
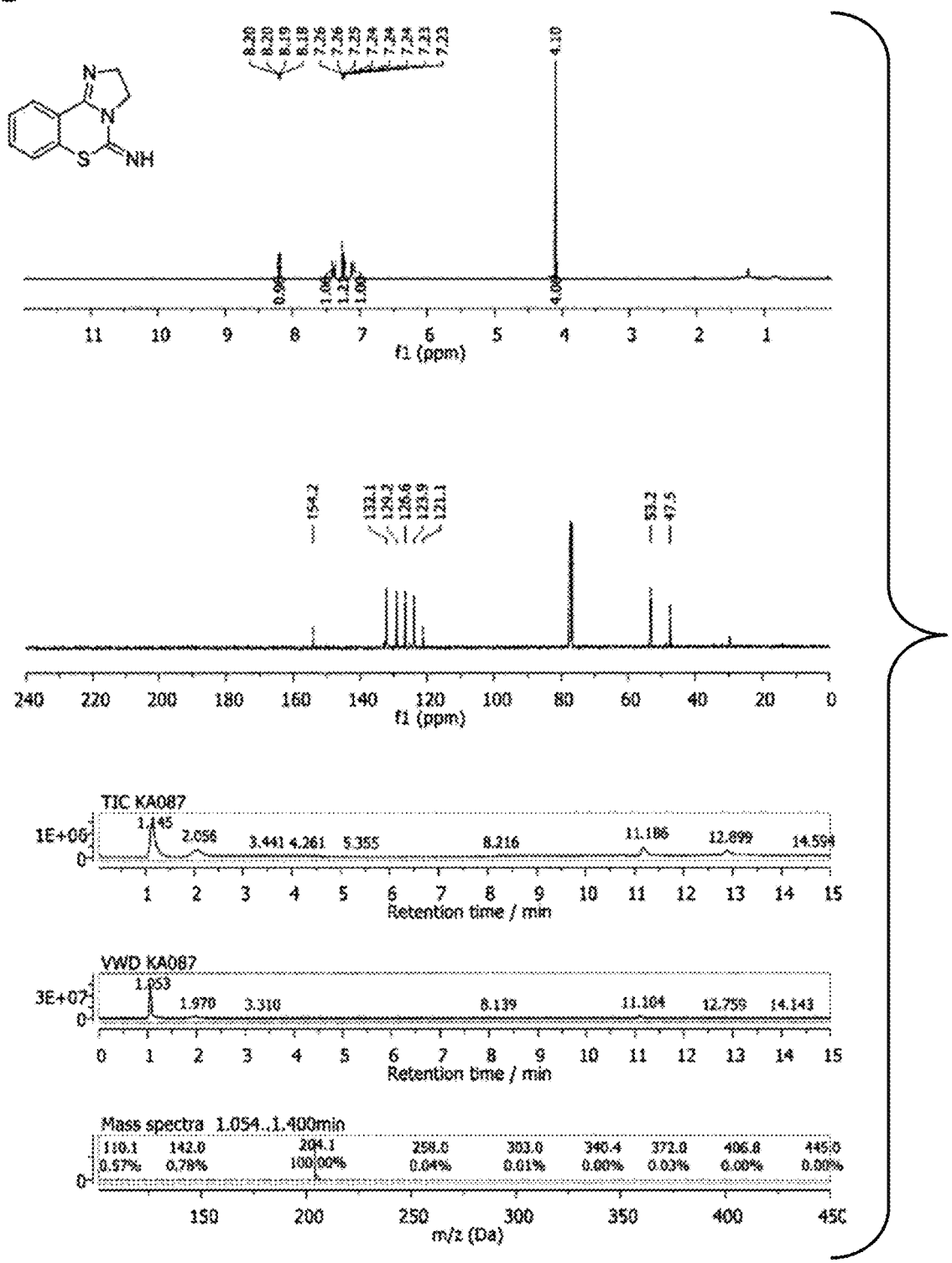
FIGS. 2A-2E—Characterization of compounds of the invention. (2A) 1H-, 13C-NMR spectra and LC/MS chromatogram of 2H-Benzo[e]imidazo[1,2-c][1,3]thiazin-5(3H)-imine (6a). (2B) 1H-, 13C-NMR spectra and LC/MS chromatogram of 9-Chloro-2H-benzo[e]imidazo[1,2-c][1,3]thiazin-5(3H)-imine (6b). (2C) 1H-, 13C-NMR spectra and LC/MS chromatogram of 6-Imino-N,N-dimethyl-2,3,4,6-tetrahydrobenzo[e]pyrimido[1,2-c][1,3]thiazin-9-amine (7c). (2D) 1H-, 13C-NMR spectra and LC/MS chromatogram of 9-Fluoro-3,4-dihydrobenzo[e]pyrimido[1,2-c][1,3]thiazin-6(2H)-imine (7d). (2E) 1H-, 13C-NMR spectra and LC/MS chromatogram of 9-Bromo-3,4-dihydrobenzo[e]pyrimido[1,2-c][1,3]thiazin-6(2H)-imine (7e).
Figure 2B:
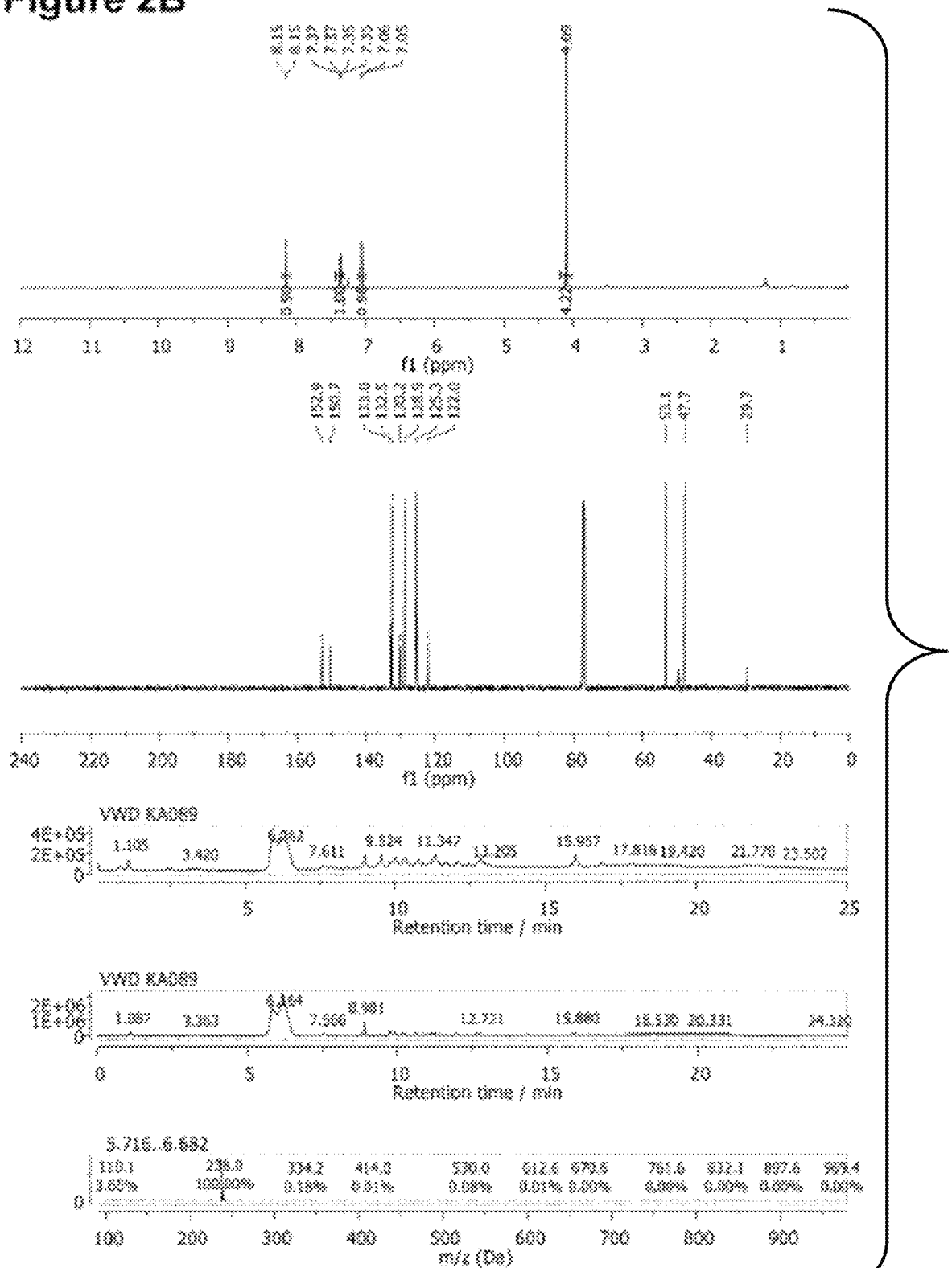
Figure 2C:
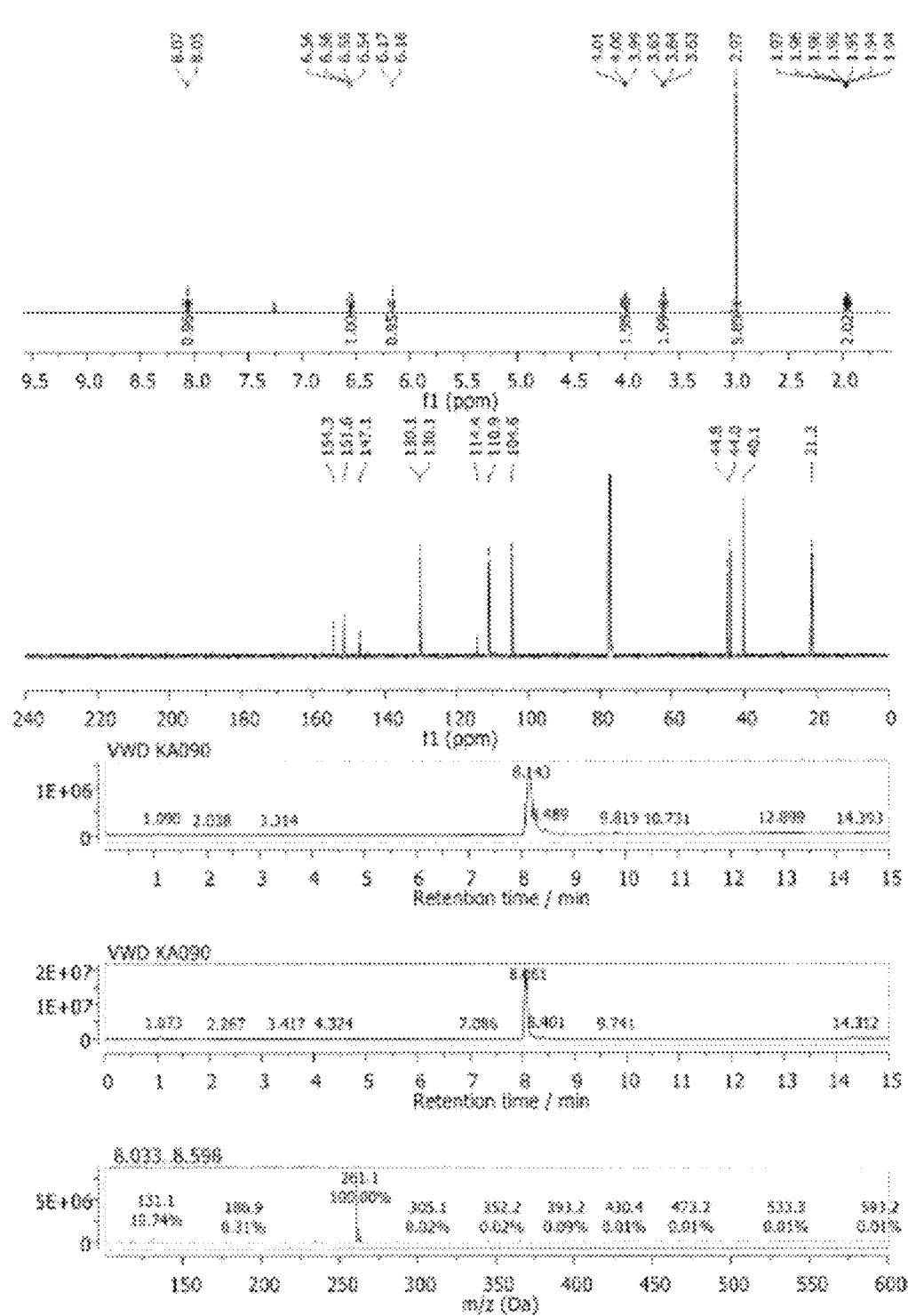
Figure 2D:
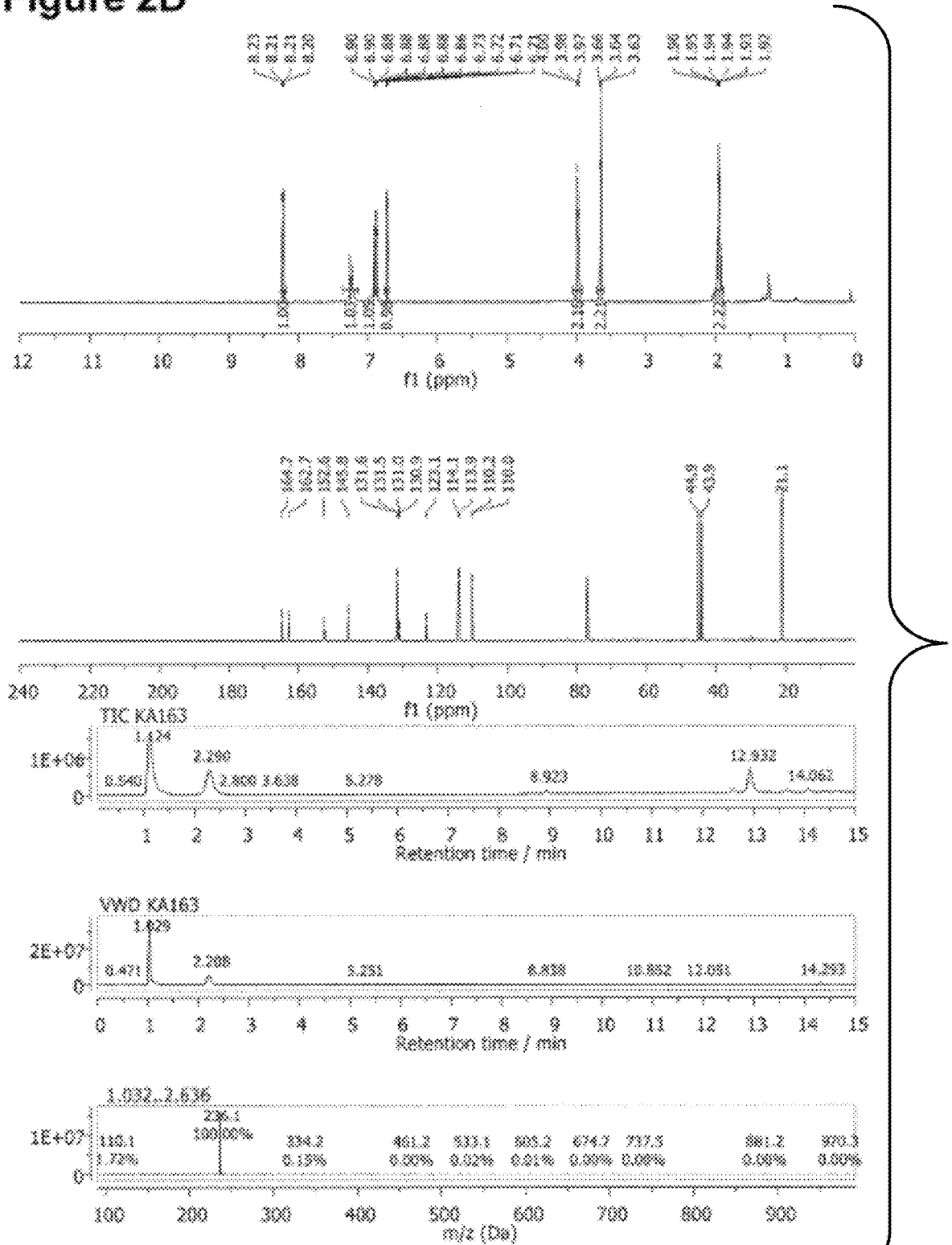
Figure 2E:
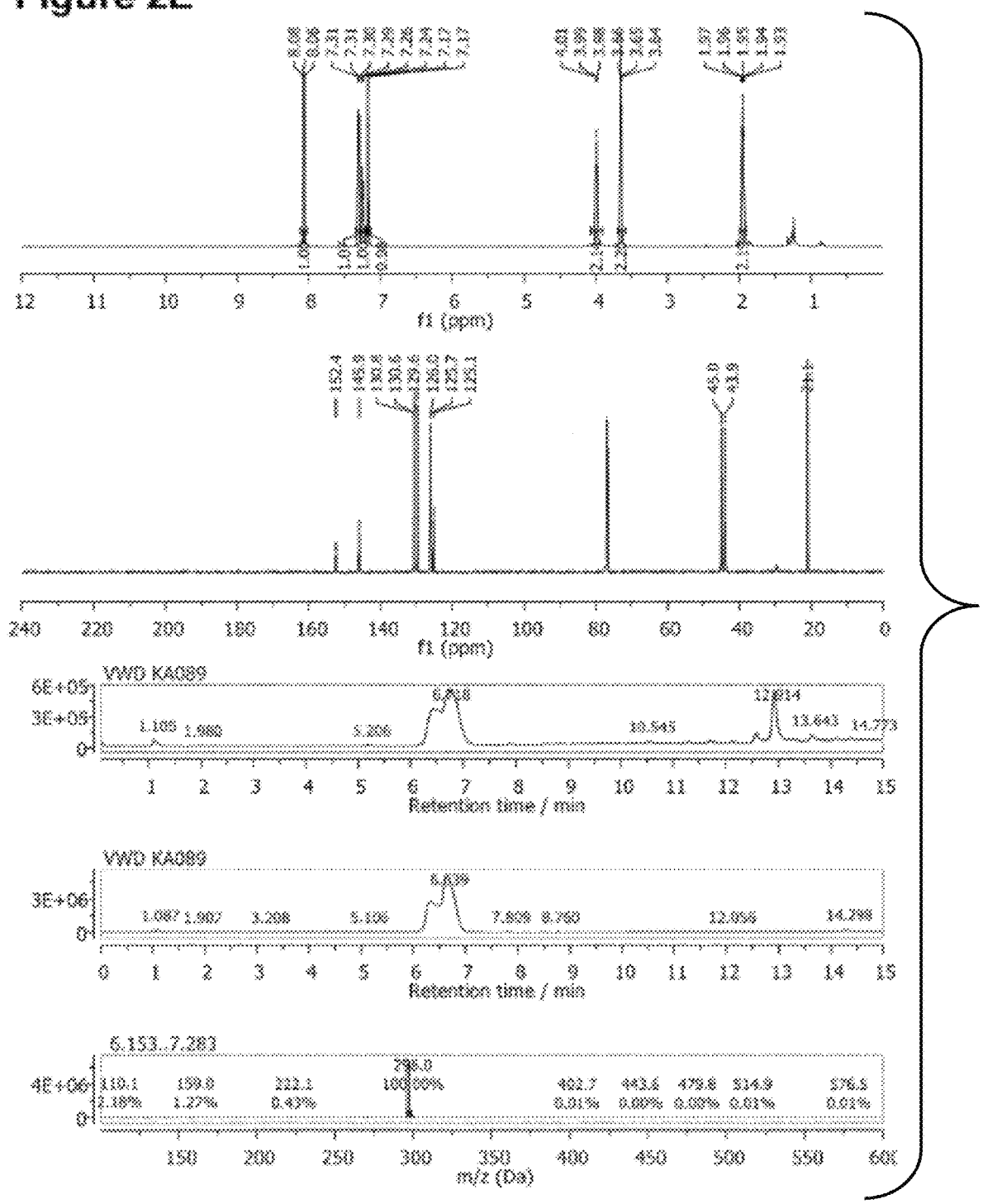
Figure 3A:
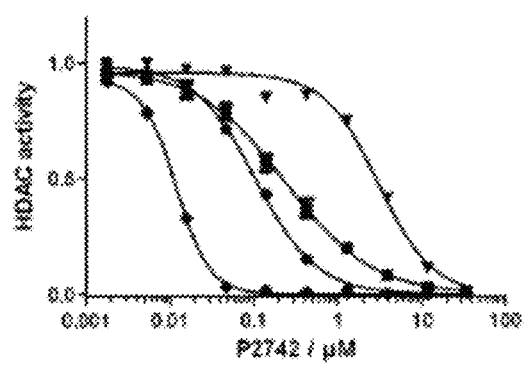
FIGS. 3A-3D—Inhibition of HDACs 1, 5, 7 and 8 by compounds of the invention. (3A) P2742, (3B) KA089 (6b), (3C) KA090 (7c), and (3D) KA091 (7b). The HDAC activity was investigated using a colorimetric assay as described by Wegener el al (2009) using 50 µM of the substrate Boc-Lys (Ac)-AMC for HDAC1 or 20 µM of the substrate Boc-Lys (TFA)-AMC for HDAC5, 7 and 8. The $IC_{50}$-values of P2742 were determined to be 3.0 µM for HDAC1, 0.11 µM for HDAC5, 0.24 µM for HDAC7 and 0.012 µM for HDAC8. For KA089 the $IC_{50}$-values were 20 µM for HDAC1, 13 µM for HDAC5, 0.51 µM for HDAC7 and 0.20 µM for HDAC8. The compound KA090 showed $IC_{50}$-values of 34 µM for HDAC1, 12 µM for HDAC5, 2.1 µM for HDAC7 and 0.071 µM for HDAC8. The $IC_{50}$-values of KA091 were 7.9 µM for HDAC1, 1.0 µM for HDAC5, 0.080 µM for HDAC7 and 0.0055 µM for HDAC8.
Figure 3B:
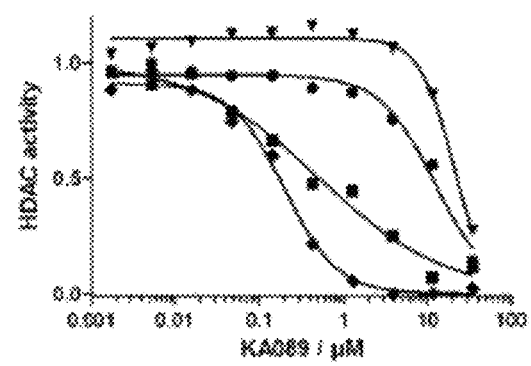
Figure 3C:
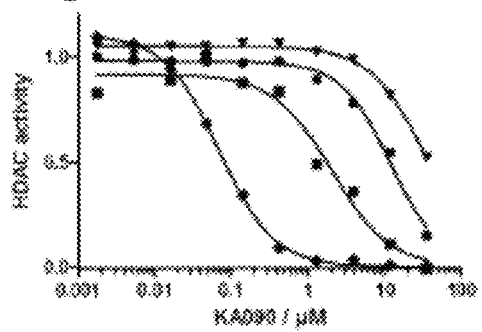
Figure 3D:
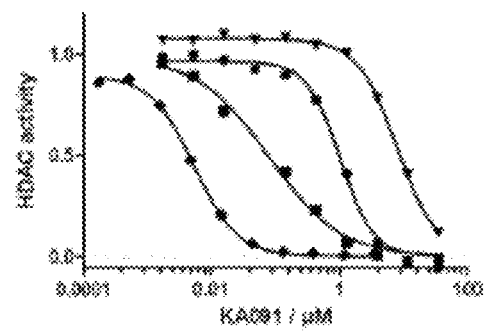
Figure 4A:
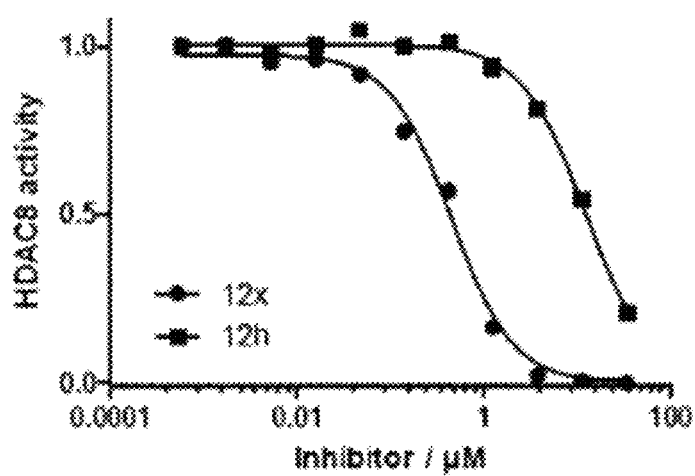
FIGS. 4A-4B—Inhibition of HDAC8 and cell proliferation of cancer cells by further compounds of the invention. (4A) The HDAC8 activity was investigated using a colorimetric assay as described by Wegener et al (2009) using 20 µM of the substrate Boc-Lys(TFA)-AMC. Increasing concentrations of the thions 12x and 12h inhibit HDAC8 with different potencies. (4B) The proliferation of JURKAT T-cell leukemia cells ($9 \times 10^4$ per well) was monitored in the presence of different compound concentrations using a resazurin reduction assay. 12x is a potent inhibitor of cell proliferation.
Figure 4B:
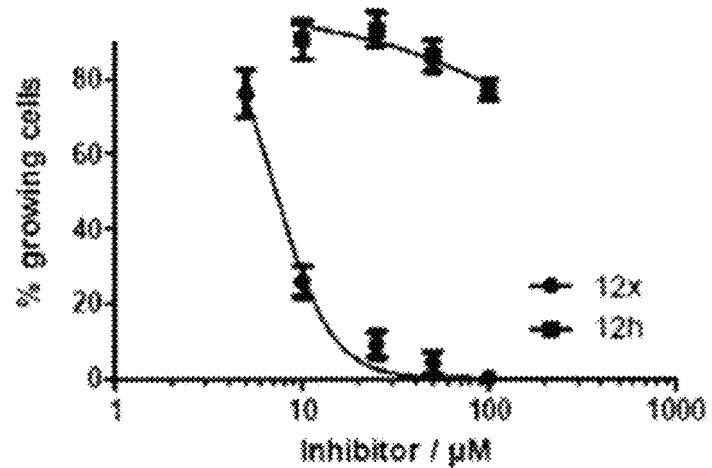

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "0.03 to 60 mg per kg" should be interpreted to include not only the explicitly recited values of 0.03 to 60, but also include individual values and sub-ranges within the indicated range. Thus, included in this numerical range are individual values such as 0.03, 0.035, 0.04, 0.045, ... 59, 60 and sub-ranges such as from 14 to 20, from 14 to 30, from 15 to 25, from 19 to 25, from 20 to 25, from 20 to 30 and from 15 to 30, etc. This same principle applies to ranges reciting only one numerical value, such as "at least 0.03 mg per kg". Furthermore, such an interpretation should apply regardless of the breadth of the range or the characteristics being described.

HDAC Inhibitory Compounds

As discussed above, the present invention provides a class of small molecule compounds and their use as HDAC inhibitors.

The here described class of HDAC inhibitors was shown to be also promising with respect to selective efficacy for target HDAC8.

A compound of the present invention is a compound having the general formula I or II or III or IV.

A compound of the present invention is a compound having the general formula I or II

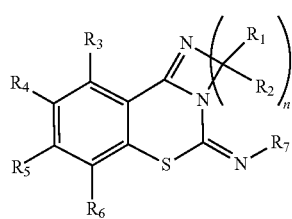
(I)

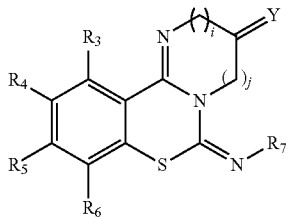
(II)

wherein
n is an integer of 1 to 7, preferably 1 to 4,
i, j are each an integer of 1 to 5, preferably 1 to 3,
Y is O, $NR_{11}$ and S,
$R_1$, $R_2$, $R_3$, $R_4$, $R_5$, $R_6$ and $R_7$ are each independently selected from hydrogen;
halogen, such as I, Cl, Br, F,
$NO_2$, CN, $SO_3$, $N(R_{10})_2$,
O—X, S—X, $NR_8$—X, —$NR_{10}$C(=O)—X, S(=O)—X, $S(=O)_2$—X, $NHS(=O)_2$—X,
$C_1$-$C_6$ alkyl-X, $C_2$-$C_6$ alkenyl-X, $C_2$-$C_6$ alkynyl-X, $C_1$-$C_6$ heteroalkyl-X, $C_1$-$C_6$ fluoroalkyl-X, partially fluorinated $C_1$-$C_6$ alkyl-X, $C_1$-$C_6$ alkyl-O—X, $C_1$-$C_3$ alkyl-O—$C_1$-$C_3$ alkyl-X, $C_1$-$C_6$ alkyl-$NR_8$—X, $C_1$-$C_3$ alkyl-$NR_8$—$C_1$-$C_3$ alkyl-X, $C_1$-$C_6$ alkyl-C(=O)$NR_8$—X, $C_1$-$C_3$ alkyl-C(=O)$NR_8$—$C_1$-$C_3$ alkyl-X, $C_1$-$C_6$ alkyl-$NR_8$C(=O)—X, $C_1$-$C_3$ alkyl-$NR_8$C(=O)—$C_1$-$C_3$ alkyl-X, $C_1$-$C_6$ alkyl-S—X, $C_1$-$C_3$ alkyl-S—$C_1$-$C_3$ alkyl-X, $C_1$-$C_6$ alkyl-S(=O)—X, $C_1$-$C_3$ alkyl-S(=O)—$C_1$-$C_3$ alkyl-X, $C_1$-$C_6$ alkyl-$S(=O)_2$—X, $C_1$-$C_3$ alkyl-$S(=O)_2$—$C_1$-$C_3$ alkyl-X, C(=O)—X, C(=O)—$NR_8$—X, C(=O)—$C_1$-$C_6$ alkyl-X, substituted or unsubstituted $C_2$-$C_{10}$ heterocycloalkyl, substituted or unsubstituted aryl, heteroaryl,
$Si_1$—$Si_3$ silyl-X, $Si_2$—$Si_4$ siloxane-X;

X is hydrogen, or a substituted or unsubstituted group selected from aryl, heteroaryl, $C_1$-$C_6$ alkyl, $C_2$-$C_6$ alkenyl, $C_1$-$C_6$ fluoroalkyl, partially fluorinated $C_1$-$C_6$ alkyl, $C_1$-$C_3$ alkylamino$C_1$-$C_3$ alkoxy, hydroxy$C_1$-$C_3$ alkylamino$C_1$-$C_3$ alkoxy, $C_2$-$C_8$ heterocycloalkyl$C_1$-$C_3$ alkoxy, $C_2$-$C_8$ heterocycloalkyl$C_1$-$C_2$ alkyl, CN, $NO_2$, $SO_3$, $CO_2R_9$, $C(=O)R_9$, S—$R_9$, S(=O)—$R_9$, $S(=O)_2$—$R_9$, $NR_{10}$C(=O)—$R_9$, $C(=O)N(R_{10})_2$, $S(=O)_2N(R_{10})_2$, $NR_{10}S(=O)_2$—$R_9$, OC(=O)$N(R_{10})_2$, $NR_{10}$C(=O)O—$R_9$, —OC(=O)O—$R_9$, NHC(=O)NH—$R_9$, OC(=O)$R_9$, $N(R_{10})_2$, $C_1$-$C_2$ alkyl$N(R_{10})_2$, $C_2$-$C_6$ alkyne, $C_1$-$C_6$ heteroalkyl, $C_3$-$C_{10}$ cycloalkyl, $C_2$-$C_{10}$ heterocycloalkyl, $Si_1$—$Si_3$ silyl, $Si_2$—$Si_4$ siloxane;

$R_8$ is selected from hydrogen, $C_1$-$C_6$ alkyl, phenyl or benzyl;

$R_9$ is a substituted or unsubstituted group selected from $C_1$-$C_6$ alkyl, $C_1$-$C_6$ fluoroalkyl, partially fluorinated $C_1$-$C_6$ alkyl, $C_3$-$C_8$cycloalkyl, $C_2$-$C_8$ heterocycloalkyl, aryl, and heteroaryl;

$R_{10}$ is hydrogen, or a substituted or unsubstituted group selected from $C_1$-$C_6$ alkyl, $C_1$-$C_6$ fluoroalkyl, partially fluorinated $C_1$-$C_6$ alkyl, $C_1$-$C_6$ heteroalkyl, $C_3$-$C_8$ cycloalkyl, $C_2$-$C_8$ heterocycloalkyl, aryl, and heteroaryl;

$R_{11}$ is hydrogen, or a substituted or unsubstituted group selected from $C_1$-$C_6$ alkyl, $C_1$-$C_6$ fluoroalkyl, partially fluorinated $C_1$-$C_6$ alkyl, $C_1$-$C_6$ heteroalkyl, $C_3$-$C_8$ cycloalkyl, $C_2$-$C_8$ heterocycloalkyl, aryl, and heteroaryl;

or a pharmaceutically accepted salt or pharmaceutically acceptable prodrug thereof.

A compound of the present invention is a compound having the general formula III or IV:

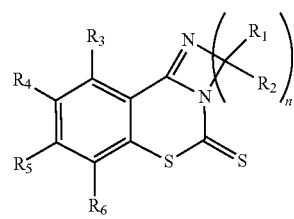
(III)

-continued

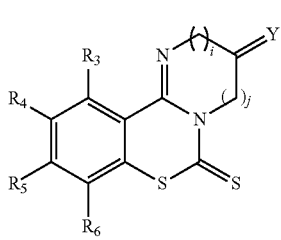

(IV)

wherein
n is an integer of 1 to 7, preferably 1 to 4,
i, j are each an integer of 1 to 5, preferably 1 to 3,
Y is O, $NR_{11}$ and S,
$R_1$, $R_2$, $R_3$, $R_4$, $R_5$, $R_6$ and $R_7$ are each independently selected from
hydrogen,
halogen, such as I, Cl, Br, F,
$NO_2$, CN, $SO_3$, $N(R_{10})_2$,
O—X, S—X, $NR_8$—X, —$NR_{10}C(=O)$—X, $S(=O)$—X, $S(=O)_2$—X, $NHS(=O)_2$—X,
$C_1$-$C_6$ alkyl-X, $C_2$-$C_6$ alkenyl-X, $C_2$-$C_6$ alkynyl-X, $C_1$-$C_6$ heteroalkyl-X, $C_1$-$C_6$ fluoroalkyl-X, partially fluorinated $C_1$-$C_6$ alkyl-X, $C_1$-$C_6$ alkyl-O—X, $C_1$-$C_3$ alkyl-O—$C_1$-$C_3$ alkyl-X, $C_1$-$C_6$ alkyl-$NR_8$—X, $C_1$-$C_3$ alkyl-$NR_8$—$C_1$-$C_3$ alkyl-X, $C_1$-$C_6$ alkyl-$C(=O)NR_8$—X, $C_1$-$C_3$ alkyl-$C(=O)$ $NR_8$—$C_1$-$C_3$ alkyl-X, $C_1$-$C_6$ alkyl-$NR_8C(=O)$—X, $C_1$-$C_3$ alkyl-$NR_8C(=O)$—$C_1$-$C_3$ alkyl-X, $C_1$-$C_6$ alkyl-S—X, $C_1$-$C_3$ alkyl-S—$C_1$-$C_3$ alkyl-X, $C_1$-$C_6$ alkyl-$S(=O)$—X, $C_1$-$C_3$ alkyl-$S(=O)$—$C_1$-$C_3$ alkyl-X, $C_1$-$C_6$ alkyl-$S(=O)_2$ —X, $C_1$-$C_3$ alkyl-$S(=O)_2$—$C_1$-$C_3$ alkyl-X, $C(=O)$—X, $C(=O)$—$NR_8$—X, $C(=O)$—$C_1$-$C_6$ alkyl-X,
substituted or unsubstituted $C_2$-$C_{10}$ heterocycloalkyl, substituted or unsubstituted aryl, heteroaryl,
$Si_1$—$Si_3$ silyl-X, $Si_2$—$Si_4$ siloxane-X;
X is hydrogen, or a substituted or unsubstituted group selected from aryl, heteroaryl, $C_1$-$C_6$ alkyl, $C_2$-$C_6$ alkenyl, $C_1$-$C_6$ fluoroalkyl, partially fluorinated $C_1$-$C_6$ alkyl, $C_1$-$C_3$ alkylamino$C_1$-$C_3$ alkoxy, hydroxy$C_1$-$C_3$ alkylamino$C_1$-$C_3$ alkoxy, $C_2$-$C_8$ heterocycloalkyl$C_1$-$C_3$ alkoxy, $C_2$-$C_8$ heterocycloalkyl$C_1$-$C_2$ alkyl, CN, $NO_2$, $SO_3$, $CO_2R_9$, $C(=O)R_9$, S—$R_9$, $S(=O)$—$R_9$, $S(=O)_2$—$R_9$, $NR_{10}C(=O)$—$R_9$, $C(=O)N(R_{10})_2$, $S(=O)_2N(R_{10})_2$, $NR_{10}S(=O)_2$—$R_9$, $OC(=O)N(R_{10})_2$, $NR_{10}C(=O)O$—$R_9$, —$OC(=O)O$—$R_9$, NHC(=O)NH—$R_9$, $OC(=O)R_9$, $N(R_{10})_2$, $C_1$-$C_2$ alkylN$(R_{10})_2$, $C_2$-$C_6$ alkyne, $C_1$-$C_6$ heteroalkyl, $C_3$-$C_{10}$cycloalkyl, $C_2$-$C_{10}$ heterocycloalkyl, $Si_1$—$Si_3$ silyl, $Si_2$—$Si_4$ siloxane;
$R_8$ is selected from hydrogen, $C_1$-$C_6$ alkyl, phenyl or benzyl;
$R_9$ is a substituted or unsubstituted group selected from $C_1$-$C_6$ alkyl, $C_1$-$C_6$ fluoroalkyl, partially fluorinated $C_1$-$C_6$ alkyl, $C_3$-$C_8$ cycloalkyl, $C_2$-$C_8$ heterocycloalkyl, aryl, and heteroaryl;
$R_{10}$ and $R_{11}$ are each independently selected from hydrogen, or a substituted or unsubstituted group selected from $C_1$-$C_6$ alkyl, $C_1$-$C_6$ fluoroalkyl, partially fluorinated $C_1$-$C_6$ alkyl, $C_1$-$C_6$ heteroalkyl, $C_3$-$C_8$ cycloalkyl, $C_2$-$C_8$ heterocycloalkyl, aryl, and heteroaryl; or a pharmaceutically accepted salt or pharmaceutically acceptable prodrug thereof, as inhibitor of enzymes of the histone deacetylase (HDAC) family.

In one embodiment, a compound of the present invention having general formula III or IV is a compound which is an intermediate/a synthesis intermediate of a compound having general formula I or II.

Examples for "$C_1$-$C_6$ alkyl" are: methyl, ethyl, n-propyl, iso-propyl, n-butyl, iso-butyl, or tert-butyl.

Examples for "$C_2$-$C_6$ alkenyl" are: ethenyl, 1-methyl-ethenyl, cis-2-methyl-ethenyl, trans-2-methyl-ethenyl, cis-1,2-dimethyl-ethenyl, trans-1,2-dimethyl-ethenyl, cis-1-propenyl, trans-1-propenyl, 2-propenyl, cis-1-butenyl, trans-1-butenyl, cis-2-butenyl, trans-2-butenyl, or 3-butenyl.

Examples for "$C_2$-$C_6$ alkynyl" are: ethynyl, 1-propynyl, 2-propynyl, 3-methyl-1-propynyl, 3,3-dimethyl-1-propynyl, 1-methyl-2-propynyl, 1,1-dimethyl-2-propynyl, 1-butynyl, 2-butynyl, or 3-butynyl.

Examples for "$C_3$-$C_{10}$ cycloalkyl" are: cyclopropyl, cyclobutyl, cyclopentyl, or cyclohexyl.

Examples for "$C_1$-$C_6$ alkoxy" are: methoxy, ethoxy, or propoxy.

Examples for "$C_2$-$C_{10}$ heterocycloalkyl" are: quinolizinyl, dioxinyl, piperidinyl, morpholinyl, thiomorpholinyl, thiazinyl, tetrahydropyridinyl, piperazinyl, oxazinanonyl, dihydropyrrolyl, dihydroimidazolyl, tetrahydrofuranyl, tetrahydropyranyl, dihydrooxazolyl, oxiranyl, pyrrolidinyl, pyrazolidinyl, dihydrothienyl, imidazolidinonyl, pyrrolidinonyl, dihydrofuranonyl, dioxolanyl, thiazolidinyl, piperidinonyl, indolinyl, tetrahydroquinolinyl, tetrahydroisoquinolinyl, or tetrahydrothienyl.

Examples for "heteroaryl" are: pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, 4-azaindolyl, 5-azaindolyl, 6-azaindolyl, 7-azaindolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothienyl, benzothiazolyl, benzoxazolyl, quinazolinyl, quinoxalinyl, imidazo[1,2-a]pyridinyl, thiophenopyridinyl, or furopyridinyl.

Examples for "$Si_1$—$Si_3$ silyl" are: trimethylsilyl, triethylsilyl, triisopropylsilyl, or tert-butyldimethylsilyl.

Examples for "$Si_2$—$Si_4$ siloxane" are: dimethylsiloxy, ethylmethylsiloxy, diisopropylsiloxy, di-tert-butylsiloxy, (trimethylsiloxy)dimethylsilyl.

The compounds of the present invention are provided as inhibitors of enzymes of the histone deacetylase (HDAC) family.

Preferably, the compounds of the present invention selectively inhibit HDAC8.

An inhibitor is "selective" as used herein if its potency (which is proportional to the inverse of $K_i$ or $IC_{50}$ values) against HDAC8 is at least 10 times higher compared to each of the other HDAC isoform.

In a preferred embodiment, in the compound having general formula I n is 2 or 3.

In this embodiment, the compounds of the present invention are based on benzopyrimido- or benzoimidazo-thiazin-imine.

For embodiments wherein n is more than 1, such as 2, 3, 4, 5, 6 or 7, optionally $R_1$ and/or $R_2$ of each C atom are different from each other.

A compound of the present invention is not P2742 (ND 404,182; 6H-6-Imino-(2,3,4,5-tetrahydropyrimido)[1,2-c]-[1,3]benzothiazine) with the following formula:

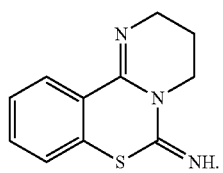 [SMILES: N=C1Sc2ccccc2C2=NCCCN12]

In a preferred embodiment, in the compound having general formula I
$R_1$ and $R_2$ are hydrogen.
In a preferred embodiment, in the compound
$R_3$, $R_4$, $R_5$ and $R_6$ are each independently selected from hydrogen, halogen (Cl, Br, F) and alkylamino.
In a preferred embodiment, in the compound
$R_7$ is hydrogen.
In One Embodiment, in the Compound
n is 2 or 3; and/or
$R_1$ and $R_2$ are hydrogen; and/or
$R_3$, $R_4$, $R_5$ and $R_6$ are each independently selected from hydrogen, halogen (Cl, Br, F) and alkylamino; and/or
$R_7$ is hydrogen.
In one embodiment, in the compound having general formula I
n is 2 or 3; and/or
$R_1$, $R_2$, $R_3$, $R_4$, $R_5$, $R_6$ and $R_7$ are each hydrogen.
In one embodiment, the compound has general formula II and
i=j.
Preferably, the Compound is Selected from 2H-Benzo[e]imidazo[1,2-c][1,3]thiazin-5(3H)-imine (6a, also named 13b) "KA087"

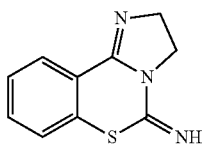 [SMILES: N=C1Sc2ccccc2C2=NCCN12]

9-Chloro-2H-benzo[e]imidazo[1,2-c][1,3]thiazin-5(3H)-imine (6b, also named 13c) "KA089"

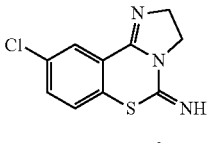

6-Imino-N,N-dimethyl-2,3,4,6-tetrahydrobenzo[e]pyrimido[1,2-c][1,3]thiazin-9-amine (7c, also named 13d) "KA090"

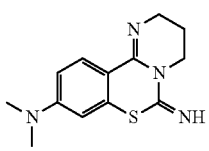 [SMILES: CN(C)c1ccc2c(c1)SC(=N)N1CCCN=C21]

10-Chloro-3,4-dihydrobenzo[e]pyrimido[1,2-c][1,3]thiazin-6(2H)-imine (7b, also named 13e) "KA091"

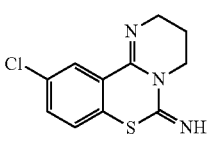 [SMILES: N=C1Sc2ccc(Cl)cc2C2=NCCCN12]

9-Fluoro-3,4-dihydrobenzo[e]pyrimido[1,2-c][1,3]thiazin-6(2H)-imine (7d, also named 13f) "KA163"

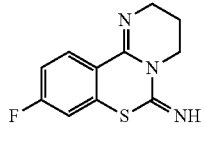

9-Bromo-3,4-dihydrobenzo[e]pyrimido[1,2-c][1,3]thiazin-6(2H)-imine (7e, also named 13g) "KA171"

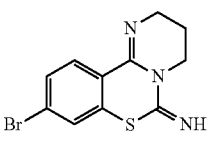 [SMILES: N=C1Sc2cc(Br)ccc2C2=NCCCN12]

8-Fluoro-3,4-dihydrobenzo[e]pyrimido[1,2-c][1,3]thiazin-6(2H)-imine (7f, also named 13h) "KA173"

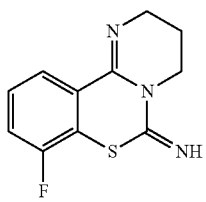 [SMILES: N=C1Sc2c(F)cccc2C2=NCCCN12]

Preferably, the compound is selected from 13b, 13c, 13d, 13e, 13f, 13g, 13 h, 13i, 13j, 13k, 13l and 13m, more preferably 13b, 13c, 13d, 13e, 13f, 13g, 13 h, 13j, 13k, 13l and 13m In a preferred embodiment, in the compound having general formula III
n is 2 or 3.
In this embodiment, the compounds of the present invention are based on benzopyrimido- or benzoimidazo-thiones.
In a preferred embodiment, in the compound having general formula III
n is 2 or 3; and/or
$R_3$, $R_4$, $R_5$ and $R_6$ are each hydrogen; and/or
of $R_3$, $R_4$, $R_5$ and $R_6$ two or three are hydrogen; and/or
$R_3$, $R_4$, $R_5$ and $R_6$ are each independently selected from hydrogen, halogen (Cl, Br, F), $C_1$-$C_6$ alkyl, alkylamino, $N(R_{10})_2$ with $R_{10}$ being $C_1$-$C_6$ alkyl, and $C_1$-$C_6$ fluoroalkyl-X with X being hydrogen.
In a preferred embodiment, the compound has general formula III and
n is 2;
$R_3$ is alkyl, preferably methyl, and
$R_4$, $R_5$, and $R_6$ are each hydrogen.
Preferably, the compound is compound 12x ("KA192").
In a preferred embodiment, the compound has general formula III and
n is 2;
$R_3$, $R_4$, and $R_5$ are each hydrogen; and
$R_6$ is halogen, preferably F.
Preferably, the compound is compound 12 h.
In a preferred embodiment, the compound has general formula III and
n is 3;
$R_3$, $R_4$, and $R_6$ are each hydrogen; and
$R_5$ is halogen, preferably Br.
Preferably, the compound is compound 12g.
In a preferred embodiment, the compound has general formula III and
n is 3;
$R_3$, $R_4$, and $R_6$ are each hydrogen; and
$R_5$ is alkyl, preferably methyl.
Preferably, the compound is compound 12k.
In a preferred embodiment, the compound has general formula III and
n is 2;
$R_3$, $R_5$, and $R_6$ are each hydrogen; and
$R_4$ is halogen, preferably Br.
Preferably, the compound is compound 12t.
In a preferred embodiment, the compound having general formula III is selected from compound 12x (KA192), 12g, 12k, 12t and 12 h.
In one embodiment, the compound has general formula IV and
i=j.

Pharmaceutical Compositions and Medical Uses

As discussed above, the present invention provides a pharmaceutical composition comprising
- (a) at least one compound according to the present invention,
- (b) optionally, pharmaceutically acceptable excipient(s) and/or carrier.

The pharmaceutical composition can optionally comprise a further agent or drug, such as cytostatic compound(s).

In one embodiment, the pharmaceutical composition is used in a combination therapy together with other anti-cancer drug(s).

Preferably, the pharmaceutical composition is for oral application/administration.

The skilled artisan can select suitable pharmaceutically acceptable excipient(s) and/or carrier for such oral application/administration.

As discussed above, the present invention provides a compound according to the present invention or the pharmaceutical composition according to the present invention for use in the treatment of cancer.

Preferably, the cancer is selected from
neuroblastoma,
T-cell lymphomas,
urothelial cancer, or
breast cancer.

Several studies clearly identified HDAC8 to be involved in various cancer diseases like T-cell lymphoma (Balasubramanian et al., 2008; U.S. Pat. No. 8,906,954), neuroblastoma (Oehme et al., 2009), urothelial cancer (Niegisch et al., 2013) and breast cancer (Park et al., 2011) as well as in neural crest development (Haberland et al., 2009).

As discussed above, the present invention provides a compound according to the present invention or the pharmaceutical composition according to the present invention for use as therapeutic agent against eukaryotic parasites.

As discussed above, the present invention provides a compound according to the present invention or the pharmaceutical composition according to the present invention for use in the treatment of infections with eukaryotic parasites.

The eukaryotic parasites are preferably *Schistosoma mansoni* or *Plasmodium falciparum*.

See e.g. Giannini et al., 2015 or Stolfa 2014.

In one embodiment, the compound or pharmaceutical composition of the present invention are used in combination with further agent(s) or drug(s), such as cytostatic compound(s).

For example, compound or pharmaceutical composition of the present invention are used in a combination therapy together with other anti-cancer drug(s).

Preferably, the medical use of the present invention comprises the administration of a therapeutically effective amount of a compound of the present invention or of a pharmaceutical composition of the present invention.

Methods for Treatment

As discussed above, the present invention provides a method of treatment of cancer.

Said treatment method comprises the step of
administering to a subject a therapeutically effective amount of a compound according to the invention or a pharmaceutical composition of the invention.

A "therapeutically effective amount" of a compound according to the invention preferably refers to the amount necessary to achieve the therapeutic outcome.

The dosage of the compounds according to the invention is carried out in the order of magnitude customary for histone deacetylases inhibitors. For example, the customary dose in the case of systemic therapy (p.o.) may be between 0.03 and 60 mg/kg body weight per day, (i. v.) may be between 0.03 and 60 mg/kg/h. In another embodiment, the customary dose in the case of systemic therapy (p.o.) is between 0.3 and 30 mg/kg per day, (i. v.) is between 0.3 and 30 mg/kg/h. The choice of the optimal dosage regime and duration of medication, particularly the optimal dose and manner of administration of the active compounds necessary in each case can be determined by a person skilled in the art on the basis of his/her expert knowledge.

Preferably, the cancer is selected from
neuroblastoma,
T-cell lymphomas,
urothelial cancer, or
breast cancer.

In one embodiment, the treatment method of the invention comprises
administering to a subject a therapeutically effective amount of a compound according to the invention or a pharmaceutical composition of the invention
in combination with further agent(s) or drug(s), such as cytostatic compound(s), as discussed above.

As discussed above, the present invention provides a method of treatment of an infection with eukaryotic parasites.

Said treatment method comprises the step of
administering to a subject a therapeutically effective amount of a compound according to the invention or a pharmaceutical composition of the invention.

A "therapeutically effective amount" of a compound according to the invention preferably refers to the amount necessary to achieve the therapeutic outcome.

The eukaryotic parasites are preferably *Schistosoma mansoni* or *Plasmodium falciparum*.

Further Description of Preferred Embodiments

The present invention discloses novel HDAC inhibitors. Furthermore, the present invention discloses pharmaceutical compositions comprising HDAC inhibitor(s) and exemplary treatment regimens for various diseases. These especially include cancer and infections with eukaryotic parasites.

The high expression values of different HDAC members in cancer cell lines and their strong influence on gene regulation led to a new approach for cancer treatments based on histone deacetylase inhibitors (HDACi's). In the last few years several types of HDACi's could be identified for the zinc-dependent HDAC classes (I, II and IV). Four main classes are established till today: hydroxamates, cyclic peptides, small fatty acids and benzamidines. Off these four, the hydroxamates are the most enlightened group until today. In general, their structure consists of a variable cap group and a metal-binding hydroxamic acid group. Both parts are connected through an aliphatic linker. This schedule is basically in accordance to the natural substrate which complexes the zinc in the active site with an acetyl group instead of the hydroxamic acid. One of the first potent hydroxamate HDACi's was isolated from *Streptomyces* bydroscopicus: Trichostation A (TSA) (Kim et al., 2000). Based on this structure, a second very potent HDACi was synthesized: Vorinostat (SAHA) (Butler et al., 2000). SAHA was one of the first HDACi that passed all clinical trials and was applied for treatment of cutaneous T-cell lymphoma (CTCL).

Several studies clearly identified HDAC8 to be involved in various cancer diseases like T-cell lymphoma (Balasubramanian et al., 2008; U.S. Pat. No. 8,906,954), neuroblastoma (Oehme et al., 2009), urothelial cancer (Niegisch et al., 2013) and breast cancer (Park et al., 2011) as well as in neural crest development (Haberland et al., 2009).

However, most of the very potent HDACi's, in particular TSA, SAHA, Panobinostat, are rather unselective inhibitors. The inhibition of several or nearly all HDACs goes along with several site effects (see also WO 2007/019116 A1). To avoid these pharmacological issues research for HDAC isoform specific inhibitors became an urgent challenge.

The here described class of HDAC inhibitors was shown to be also promising with respect to selective efficacy hitting predominantly the wanted target HDAC8.

The class of compounds discloses herein are more potent and selective inhibitors for HDAC8 when compared to the known HDAC8-selective inhibitor PCI-34051, and also more effective on cancer cell lines.

By choosing the substituents on general formula I (or general formula II) and/or choosing the size of the ring structure (n in general formula I), the selectivity of the compounds for the HDACs and their efficacy against cancer cells can be selected and fine-tuned.

Also compounds of general formula III or IV, which can be intermediates/synthesis intermediates of the compounds having general formula I or II, are selective HDAC8 inhibitors, which in addition show higher cell stability.

Figure 6A:
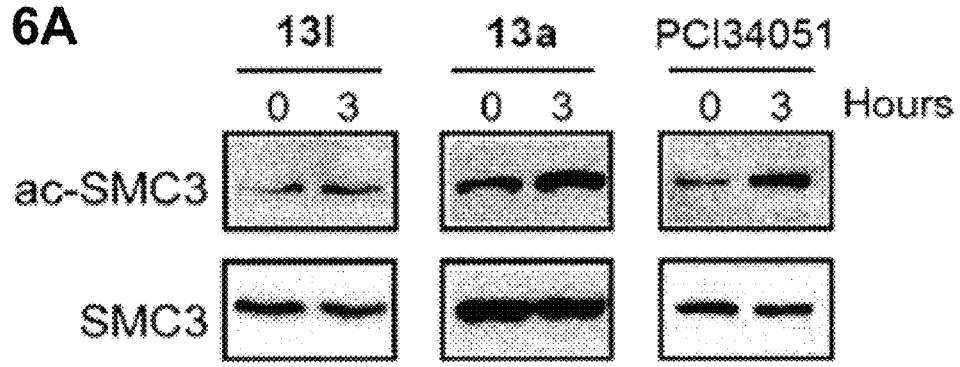
FIGS. 6A-6C—HDAC8 inhibition increases the acetylation level of SMC3, a specific substrate of HDAC8. (6A) Immunoblot analysis of acetylated SMC3 levels in Jurkat cells ($5 \times 10^5$) treated for 3 h with the indicated HDAC inhibitors. Each compound was used at its gIC50, (6B) Densitometric analysis of the acSMC3/SMC3 ratio in JURKAT cells treated as in A. n=3, *p<0.05, p<0.01, *p<0.005, the data prove the intracellular target engagement of the compounds. (6C) Immunoblot analysis of acetylated SMC3 levels in Jurkat cells ($5 \times 10^5$) treated for 0, 3, 6, 9 h with the indicated HDAC inhibitors. Each compound was used at its gIC50.
Figure 6B:
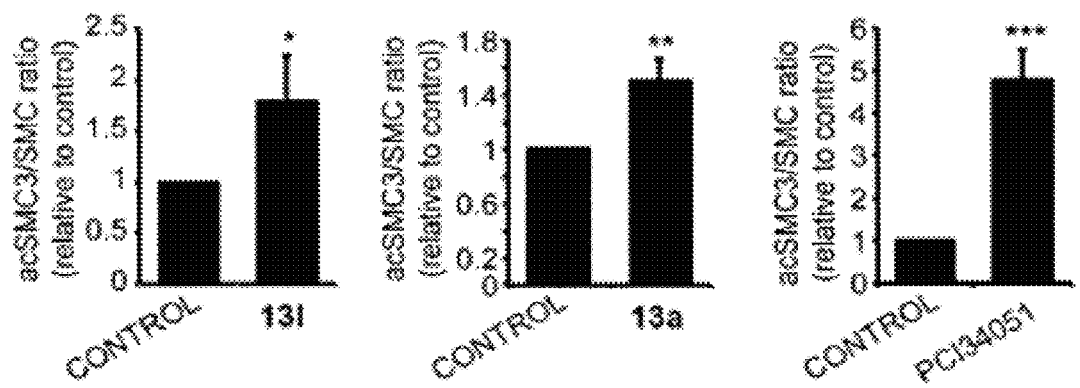
Figure 6C:
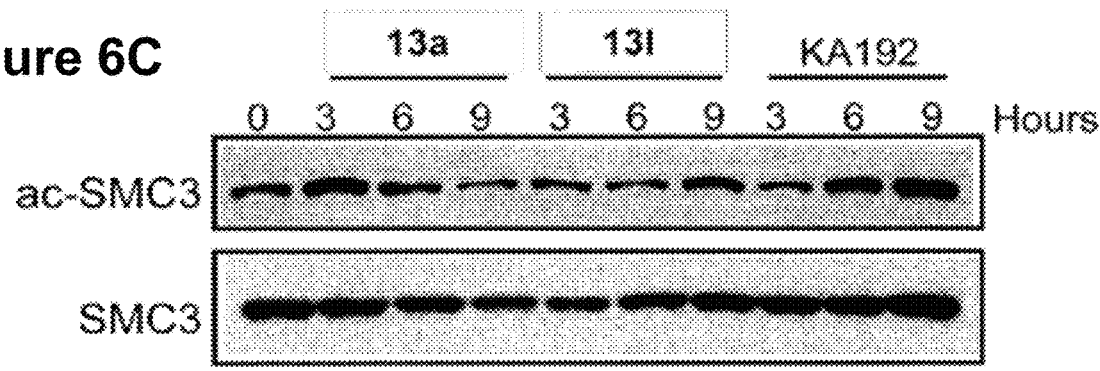
Figure 7:
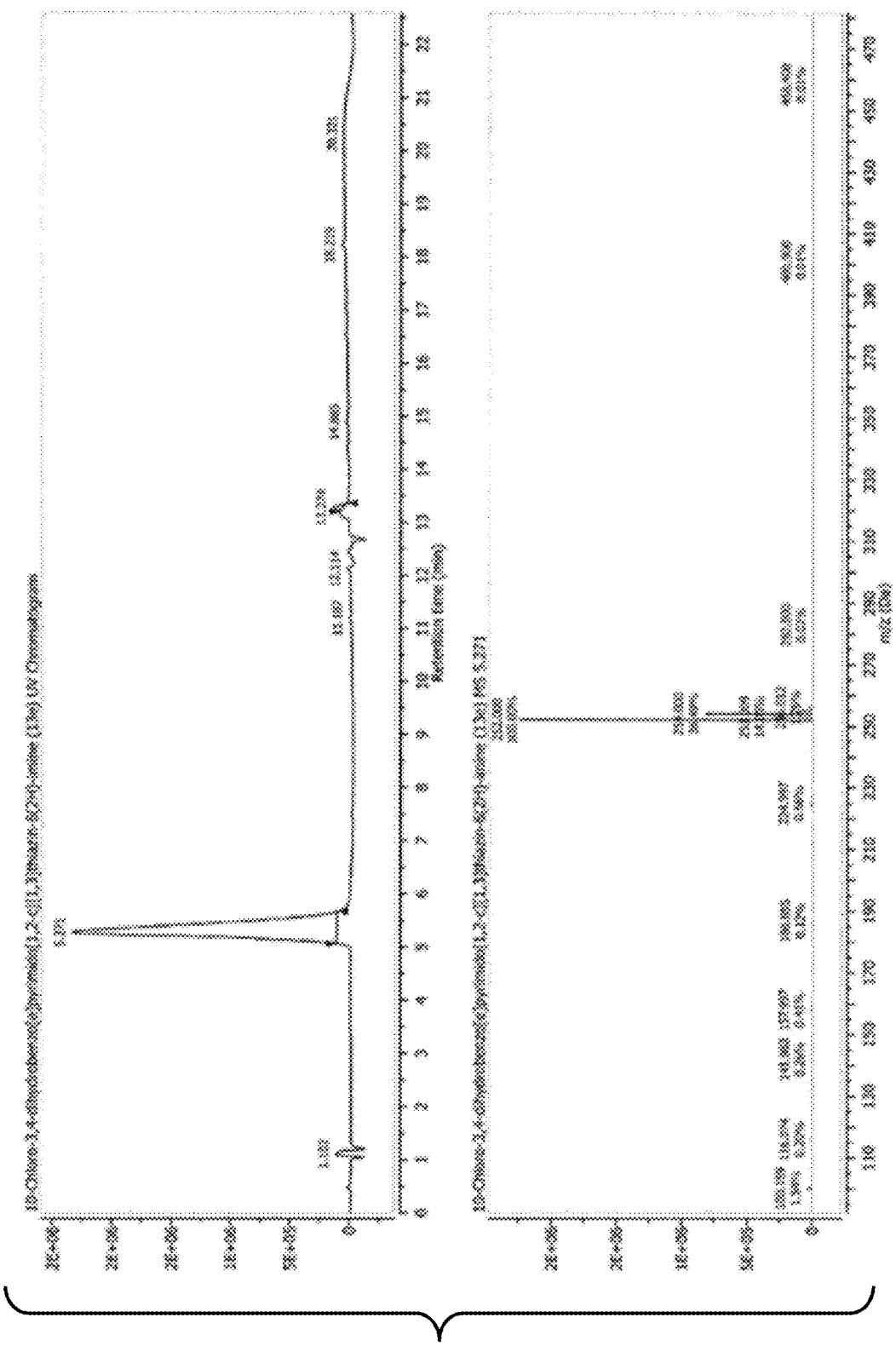
FIGS. 7A-7C—HPLC-MS of representative compounds (13e, 13g, 13i).
Figure 7:
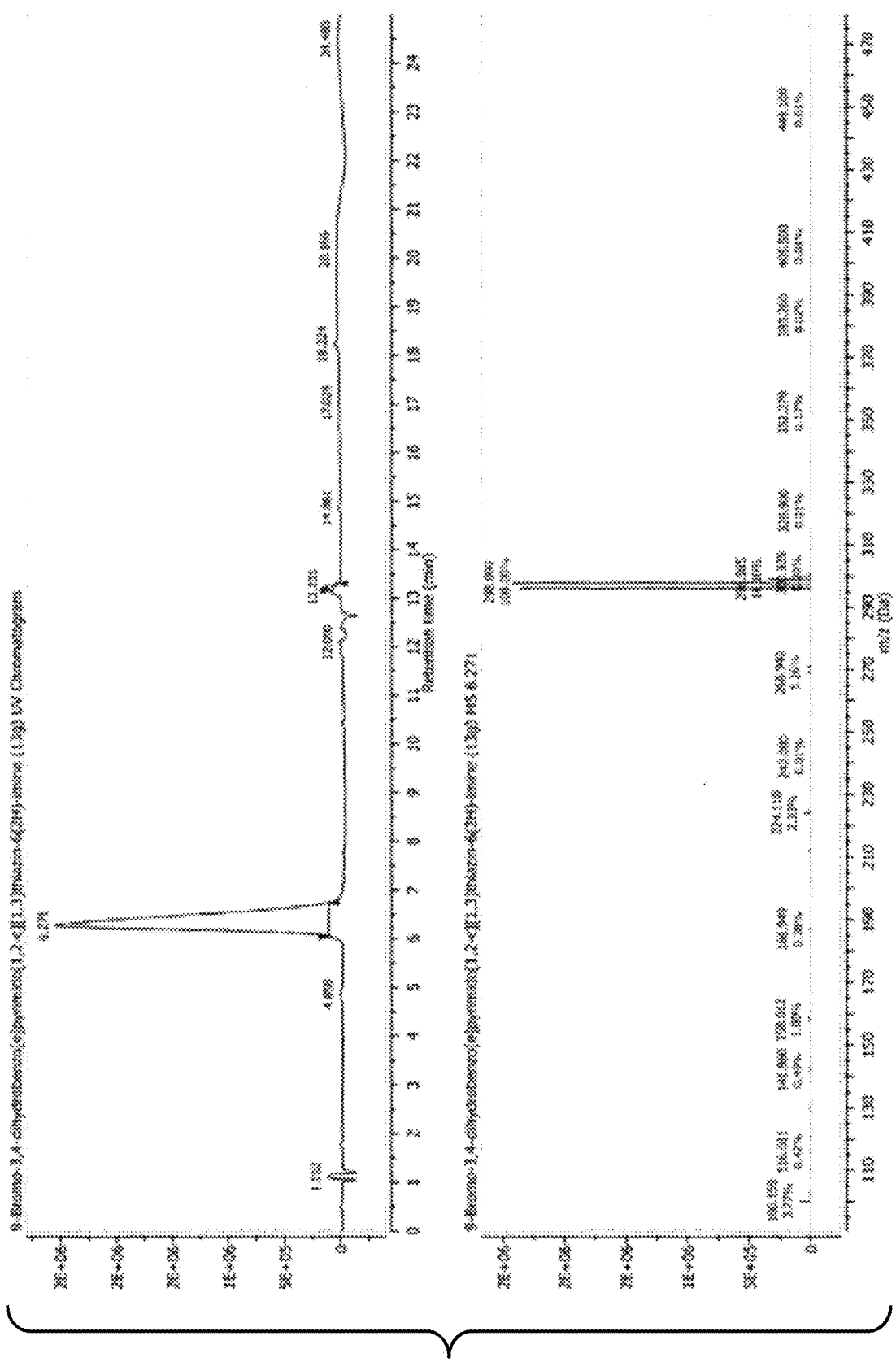
Figure 7:
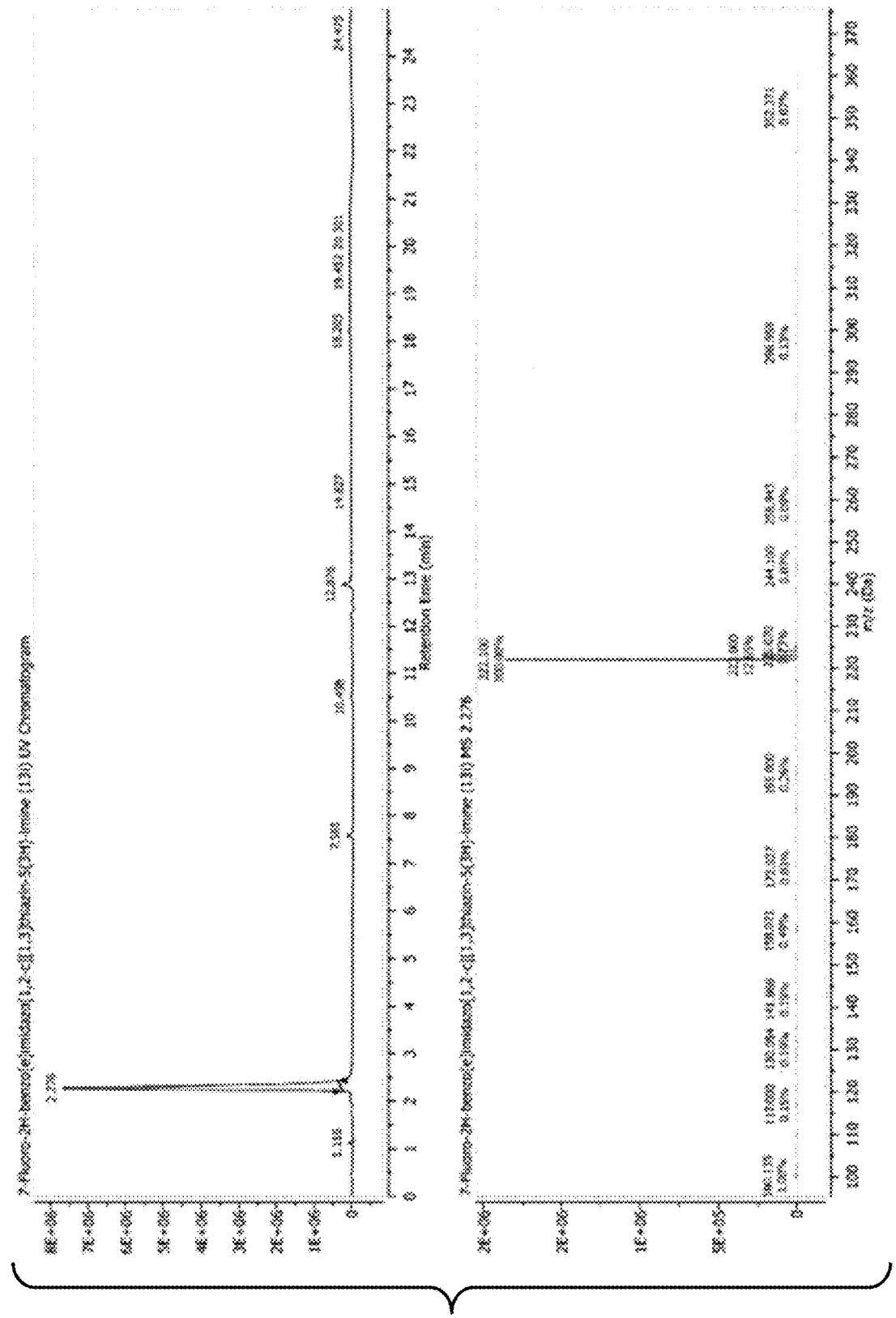

The example of the thione 12x shows that this compound is only 10 times less active against JURKAT T-cell lymphoma cancer cells (IC50=5 µM) than on the isolated HDAC8 enzyme (IC50=0.5 µM). In contrast, 13a as a representative of the imine compounds is even more potent on HDAC8 (IC50=0.011 µM) but more than 5700 time less active against JURKAT cells (GI=63 µM). This extraordinary loss in activity is attributed to decreased chemical stability of 13a in living cells. In addition, 12x increases SMC3 acetylation much stronger than the imine compounds 13a and 13l (see FIG. 6C) indicating an increased inhibition of HDAC8 within cells.

The following examples and drawings illustrate the present invention without, however, limiting the same thereto.

EXAMPLES

Example 1 Materials and Methods 1.1 All of the starting materials were obtained commercially and were used without further purification. All of the reported yields are for isolated products and are not optimized. Nuclear magnetic resonance ($^1$H and $^{13}$C NMR) spectra were recorded with a Bruker DRX-500 spectrometer (operating at 500 MHz), with chemical shifts in parts per million (δ) downfield from TMS, the internal standard. Mass spectral (MS) data were obtained using an Agilent 6110 Quadrupole LC/MS system with a 0.3 mL/min flow rate using a gradient mobile phase consisting of 0.1% trifluoroacetic acid (TFA) in water and 0.1% TFA in acetonitrile. UV detection was monitored at 227 nm. Mass spectra were acquired either in positive or in negative mode scanning over the mass range of 105-1500. The purities of the final compounds were determined using an Agilent 1200 series HPLC system using a C-18 column (Waters Sunfire C18 3.5 µm, 2.1 mm×100 mm) and were found to be ≥95%. Flash column chromatography was conducted using silica gel (Merck Kieselgel 60, No. 9385, 230-400 mesh ASTM). Gas chromatographic data were obtained using an Agilent 7890A GC System (G3440A) with a mass detector VL MSD with Triple-Axis Detector (5975C) and an Agilent HP-5 MS column (19091S-433 30 m, 0.25 mm, 0.25 µm).

1.2 Tumor Cell Lines

The following tumor cell lines were used:

Human uterine leiomyosarcoma cell line SKUT-1 (ATCC® HTB114™)

Human T cell leukemia cell line JURKAT (ATCC® TIB152™)

Human breast cancer cell line MCF-7 (ATCC® HTB22™)

Cells were cultured in Dulbecco's modified Eagle's medium (DMEM) supplemented with 10% FCS.

1.3 Substances

The following commercially available substances and compounds were used: Compound P2742 (ND 404,182 of Sigma Aldrich).

1.4 Assays

Colormetric assay

As described by Wegener et al. (2003).

Resazurin assay

As described by Nociari et al. (1998).

Example 2 Chemical Synthesis and Structures

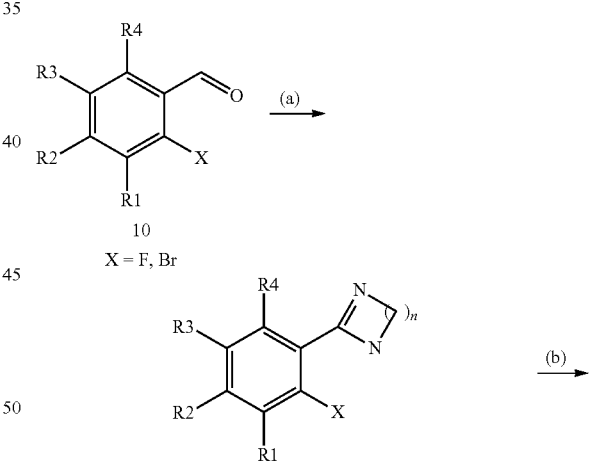

11a, n = 3, R1 = H, R2 = H, R3 = H, R4 = H, X = Br
11b, n = 2, R1 = H, R2 = H, R3 = H, R4 = H, X = Br
11c, n = 2, R1 = H, R2 = H, R3 = Cl, R4 = H, X = Br
11d, n = 3, R1 = H, R2 = N(CH$_3$)$_2$, R3 = H, R4 = H, X = Br
11e, n = 3, R1 = H, R2 = F, R3 = Cl, R4 = H, X = Br
11f, n = 3, R1 = H, R2 = F, R3 = H, R4 = H, X = F
11g, n = 3, R1 = H, R2 = Br, R3 = H, R4 = H, X = F
11h, n = 3, R1 = F, R2 = H, R3 = H, R4 = H, X = F
11i, n = 2, R1 = F, R2 = H, R3 = H, R4 = H
11j, n = 3, R1 = H, R2 = H, R3 = H, R4 = Br
11k, n = 3, R1 = H, R2 = CH$_3$, R3 = H, R4 = H
11l, n = 3, R1 = H, R2 = H, R3 = F, R4 = H
11m, n = 3, R1 = H, R2 = H, R3 = H, R4 = CH$_3$

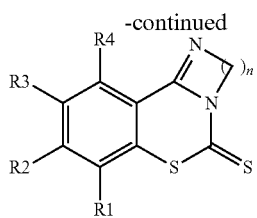

12a, n = 3, R1 = H, R2 = H, R3 = H, R4 = H
12b, n = 2, R1 = H, R2 = H, R3 = H, R4 = H
12c, n = 2, R1 = H, R2 = H, R3 = Cl, R4 = H
12d, n = 3, R1 = H, R2 = N(CH$_3$)$_2$, R3 = H, R4 = H
12e, n = 3, R1 = H, R2 = F, R3 = Cl, R4 = H
12f, n = 3, R1 = H, R2 = F, R3 = H, R4 = H
12g, n = 3, R1 = H, R2 = Br, R3 = H, R4 = H
12h, n = 3, R1 = F, R2 = H, R3 = H, R4 = H
12i, n = 2, R1 = F, R2 = H, R3 = H, R4 = H
12j, n = 3, R1 = H, R2 = H, R3 = H, R4 = Br
12k, n = 3, R1 = H, R2 = CH$_3$, R3 = H, R4 = H
12l, n = 3, R1 = H, R2 = H, R3 = F, R4 = H
12m, n = 3, R1 = H, R2 = H, R3 = H, R4 = CH$_3$

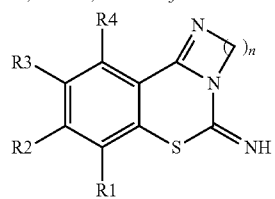

13a, n = 3, R1 = H, R2 = H, R3 = H, R4 = H
13b, n = 2, R1 = H, R2 = H, R3 = H, R4 = H
13c, n = 2, R1 = H, R2 = H, R3 = Cl, R4 = H
13d, n = 3, R1 = H, R2 = N(CH$_3$)$_2$, R3 = H, R4 = H
13e, n = 3, R1 = H, R2 = H, R3 = Cl, R4 = H
13f, n = 3, R1 = H, R2 = F, R3 = H, R4 = H
13g, n = 3, R1 = H, R2 = Br, R3 = H, R4 = H
13h, n = 3, R1 = F, R2 = H, R3 = H, R4 = H
13i, n = 2, R1 = F, R2 = H, R3 = H, R4 = H
13j, n = 3, R1 = H, R2 = H, R3 = H, R4 = Br
13k, n = 3, R1 = H, R2 = CH$_3$, R3 = H, R4 = H
13l, n = 3, R1 = H, R2 = H, R3 = F, R4 = H
13m, n = 3, R1 = H, R2 = H, R3 = H, R4 = CH$_3$ (a) ethylene diamine or 1,3-diaminopropane, K$_2$CO$_3$, I$_2$;
(b) CS$_2$, NaH;
(c) (i) NaOH in MeOH:H2O (ii) BrCN Scheme 1: Synthesis of pyrimido[1,2-c][1,3]benzothiazin-6-imines and imidazo[1,2-c][1,3]benzothiazin-6-imines for SAR studies.

2.1 General Synthesis of the 2-aryl-4,5-dihydro-1H-imidazole (11, n=2) and 2-aryl-1,4,5,6-tetrahydropyrimidine (11, n=3)

To a solution of the aldehyde 10 (1 eq.) in tert-butanol (9.0 ml/mmol) the diamine (1.1 eq.) was added and the solution was stirred at 70° C. for 30 min. K$_2$CO$_3$ (4 eq.) and I$_2$ (1.25 eq.) was added at 70° C. and the mixture was stirred at this temperature for further 3 h. The mixture was cooled down to rt and Na$_2$S$_2$O$_3$ was added until the iodine color almost disappear. The organic layer was separated and the solvent was removed in vacuo. The received solid was dissolved in water (7.5 ml/mmol) and 2N NaOH, was added until pH=12-14. The aqueous layer was separated with CHCl$_3$ (3×3.75 ml/mmol), the combined organic layers were dried (Na$_2$SO$_4$) and the solvent was removed in vacuo. The product can be used without further purification.

2-(2-Bromophenyl)-1,4,5,6-tetrahydropyrimidine (11a)

2-Bromobenzaldehyde (10a) (1 ml, 8.56 mmol) and 1,3 diaminopropane (0.785 ml, 9.42 mmol) were dissolved in t-BuOH (86 ml) and stirred for 30 min at 70° C., then Na$_2$CO$_3$ (2.72 g, 25.7 mmol) and I$_2$ (2.72 g, 10.7 mmol) were added and the mixture was stirred 3 h at the same temperature. Afterwards Na$_2$SO$_3$ sat. was added until the organic layer turns slightly yellow. The organic layer was separated and concentrated in vacuo. The obtained bright yellow solid was dissolved in 100 ml water followed by addition of 1 M NaOH till pH 13. The mixture was extracted (2×60 ml CHCl$_3$), the combined organics were dried over Na$_2$SO$_4$, filtered and concentrated to obtain a yellow oil. After recrystallization (CHCl$_3$-hexane) the title compound was obtained as a white solid (970 mg, 47%). $^1$H NMR (300 MHz, CDCl$_3$) δ 7.53-7.47 (m, 1H, Ar), 7.35-7.23 (m, 2H, Ar), 7.23-7.14 (m, 1H, Ar), 5.82 (s, 1H, NH), 3.28 (t, 4H, 2×CH$_2$), 1.86-1.64 (m, 2H, CH$_2$). $^{13}$C NMR (75 MHz, CDCl$_3$) δ 155.84, 138.53, 132.88, 130.40, 130.28, 127.51, 120.87, 41.86, 20.37.

2-(2-Bromophenyl)-4,5-dihydro-1H-imidazole (11b)

2-Bromobenzaldehyde (10a) (924 mg, 5.00 mmol) was subjected to general procedure, using ethane-1,2-diamine (367 µL, 330 mg, 5.50 mmol), K$_2$CO$_3$ (2.07 g, 15.0 mmol) and I$_2$ (1.74 g, 6.85 mmol). 2-(2-bromophenyl)-4,5-dihydro-1H-imidazole (11b) was received as orange oil (926 mg, 4.11 mmol, 82%). GC/MS (t$_r$=16.81 min, 70 eV, EI) m/z (%)=226 [M$^+$] (46), 224 [M$^+$] (48), 197 (98), 195 (100), 116 (50), 89 (39). $^1$H-NMR (CDCl$_3$, 300 MHz): δ=7.55 (td, J=7.9, 1.6 Hz, 2H), 7.32-7.18 (m, 2H), 3.72 (s, 4H). $^{13}$C-NMR (CDCl$_3$, 75 MHz): δ=164.5, 133.2, 132.7, 131.1, 131.1, 127.4, 120.8, 50.3.

2-(2-Bromo-5-chlorophenyl)-4,5-dihydro-1H-imidazole (11c)

2-Bromo-5-chlorobenzaldehyde (10c) (878 mg, 4.00 mmol) was subjected to general procedure, using ethane-1,2-diamine (294 µL, 265 mg, 4.40 mmol K$_2$CO$_3$ (1.66 g, 12.0 mmol) and I$_2$ (1.27 g, 5.00 mmol). 2-(2-bromo-5-chlorophenyl)-4,5-dihydro-1H-imidazole (11c) was received as yellowish solid (876 mg, 3.38 mmol, 84%). GC/MS (t$_r$=18.78 min, 70 eV, EI) m/z (%)=260 [M$^+$] (42), 258 [M$^+$] (33), 231 (100), 229 (78), 150 (23). $^1$H-NMR (CDCl$_3$, 500 MHz): δ=7.61 (d, J=2.6 Hz, 1H), 7.47 (d, J=8.6 Hz, 1H), 7.20 (dd, J=8.6, 2.6 Hz, 1H), 3.74 (s, 4H). $^{13}$C-NMR (CDCl3, 125 MHz): δ=163.3, 134.4, 133.6, 131.2, 131.1, 118.7, 50.6.

2-(2-Bromo-4-dimethylaminophenyl)-1,4,5,6-tetrahydropyrimidine (11d)

2-Bromo-4-dimethylaminobenzaldehyde (10d) (458 mg, 2.01 mmol) was subjected to general procedure, using propane-1,3-diamine (183 µL, 163 mg, 2.20 mmol) K$_2$CO$_3$ (829 mg, 6.00 mmol) and I$_2$ (637 mg, 2.50 mmol). 2-(2-Bromo-4-dimethylaminophenyl)-1,4,5,6-tetrahydropyrimidine (11d) was received as brown solid (564 mg, 2.00 mmol, 99%). GC/MS (t$_r$=23.21 min, 70 eV, EI) m/z (%)=283 [M$^+$] (74), 282 [M$^+$–H] (83), 281 [M$^+$] (77), 280 [M$^+$–H] (76), 225 (61), 202 (100), 145 (21). $^1$H-NMR (CDCl$_3$, 500 MHz): δ=7.21 (d, J=8.6 Hz, 1H), 6.75 (d, J=2.5 Hz, 1H), 6.55 (dd, J=8.6, 2.6 Hz, 1H), 3.39-3.26 (m, 2H), 2.92 (s, 3H), 1.76 (t, J=5.8 Hz, 3H). $^{13}$C-NMR (CDCl$_3$, 125 MHz): δ=156.1, 151.5, 130.8, 125.6, 121.4, 115.5, 110.9, 41.8, 40.2, 20.4.

2-(2-Bromo-5-chlorophenyl)-1,4,5,6-tetrahydropyrimidine (11e)

2-Bromo-5-chlorobenzaldehyde (10c) (878 g, 4.00 mmol) was subjected to general procedure, using propane-1,3-diamine (367 ml, 327 mg, 4.41 mmol), K$_2$CO$_3$ (1.66 g, 12.0 mmol) and I$_2$ (1.30 g, 5.12 mmol). 2-(2-Bromo-5-chlorophenyl)-1,4,5,6-tetrahydropyrimidine (11e) was received as yellow solid (992.7 mg, 3.63 mmol, 91%). $^1$H-NMR (CDCl$_3$, 500 MHz): δ=7.42 (d, J=8.5 Hz, 12H), 7.36 (d, J=2.6 Hz, 11H), 7.28-7.24 (m, 2H), 7.14 (dd, J=8.5, 2.6 Hz, 12H), 4.97 (s, 13H), 3.40-3.33 (m, 50H), 1.84-1.75 (m, 25H). $^{13}$C-NMR (CDCl3, 125 MHz): δ=154.4, 140.4, 134.0, 133.5, 130.4, 130.2, 118.7, 42.2, 20.5.

2-(2,4-Difluorophenyl)-1,4,5,6-tetrahydropyrimidine (11f)

2,4-Difluorobenzaldehyde (10f) (1.43 g, 10.0 mmol) was subjected to general procedure, using propane-1,3-diamine (916 μL, 815 mg, 11.0 mmol), K$_2$CO$_3$ (4.15 g, 30.0 mmol) and I$_2$ (3.18 g, 12.5 mmol). 2-(2,4-Difluorophenyl)-1,4,5,6-tetrahydropyrimidine (11f) was received as brown solid (1.73 g, 8.80 mmol, 88%). GC/MS (t$_r$=14.63 min, 70 eV, EI) m/z (%)=196 (62) [M$^+$], 195 (86) [M$^+$–H], 177 (69), 140 (100), 139 (46), 120 (39). $^1$H NMR (500 MHz, CDCl$_3$) δ 7.71 (td, J=8.8, 6.6 Hz, 1H), 6.87-6.81 (m, 1H), 6.74 (ddd, J=11.3, 8.7, 2.5 Hz, 1H), 5.74 (s, 1H), 3.49-3.33 (m, 4H), 1.98-1.58 (m, 2H). $^{13}$C NMR (126 MHz, CDCl$_3$) δ 163.5 (dd, J=251.9, 12.3 Hz), 160.3 (dd, J=250.5, 12.0 Hz), 151.3 (s), 131.9 (dd, J=9.7, 4.6 Hz), 120.4 (d, J=11.8 Hz), 111.8 (dd, J=21.2, 3.1 Hz), 104.1 (t, J=26.4 Hz), 42.00 (s), 20.5 (s).

2-(4-Bromo-2-fluorophenyl)-1,4,5,6-tetrahydropyrimidine (11g)

4-Bromo-2-fluorobenzaldehyde (10g) (5.08 g, 25.0 mmol) was subjected to general procedure, using propane-1,3-diamine (2.29 ml, 2.04 g, 27.5 mmol), K$_2$CO$_3$ (10.4 g, 75.0 mmol) and I$_2$ (7.98 g, 31.4 mmol). 2-(4-Bromo-2-fluorophenyl)-1,4,5,6-tetrahydropyrimidine (11g) was received as brown solid (800 mg, 3.11 mmol, 12%). $^1$H-NMR (CDCl$_3$, 500 MHz): δ=7.61 (t, J=8.3 Hz, 1H), 7.25 (dd, J=8.4, 1.9 Hz, 1H), 7.20 (dd, J=10.9, 1.8 Hz, 1H), 5.38 (s, 1H), 3.43 (t, J=5.8 Hz, 4H), 1.81 (p, J=5.8 Hz, 2H). $^{13}$C-NMR (CDCl3, 125 MHz): δ=159.78 (d, J=252.3 Hz), 151.12 (s), 131.76 (d, J=3.6 Hz), 127.79 (d, J=3.0 Hz), 123.76 (d, J=10.0 Hz), 123.29 (d, J=11.7 Hz), 119.55 (d, J=26.9 Hz), 42.13 (s), 20.53 (s).

2-(2,3-Difluorophenyl)-1,4,5,6-tetrahydropyrimidine (11h)

2,3-Difluorobenzaldehyde (10 h) (1.43 g, 10.0 mmol) was subjected to general procedure, using propane-1,3-diamine (916 μl, 815 mg, 11.0 mmol), K$_2$CO$_3$ (4.15 g, 30.0 mmol) and I$_2$ (3.16 g, 12.5 mmol). 2-(2,3-Difluorophenyl)-1,4,5,6-tetrahydropyrimidine (11 h) was received as brown solid (1.35 mg, 6.89 mmol, 69%). $^1$H-NMR (CDCl$_3$, 500 MHz): δ=7.36 (ddt, J=7.9, 6.3, 1.7 Hz, 1H), 7.13 (dtd, J=9.9, 8.3, 1.7 Hz, 1H), 7.02 (tdd, J=8.2, 4.8, 1.5 Hz, 1H), 5.95 (s, 1H), 3.40 (t, J=5.8 Hz, 4H), 1.80 (p, J=5.8 Hz, 2H). $^{13}$C-NMR (CDCl3, 125 MHz): δ=151.3 (d, J=2.6 Hz), 151.7-149.1 (m), 147.4 (d, J=13.9 Hz), 126.2 (d, J=8.9 Hz), 125.0 (s), 124.2 (dd, J=6.0, 5.0 Hz), 118.2 (d, J=17.1 Hz), 41.9 (s), 20.3 (s).

2-(2,3-Difluorophenyl)-4,5-dihydro-1H-imidazole (11i)

2,3-Difluorobenzaldehyde (10 h) (1.43 g, 10.0 mmol) was subjected to general procedure, using ethane-1,2-diamine (735 μL, 661 mg, 11.0 mmol K$_2$CO$_3$ (4.13 g, 30.1 mmol) and I$_2$ (3.19 g, 12.6 mmol). 2-(2,3-difluorophenyl)-4,5-dihydro-1H-imidazole (11i) was received as yellowish solid (1.55 g, 8.51 mmol, 85%). GC/MS (t$_r$=13.55 min, 70 eV, EI) m/z (%)=182 [M$^+$] (38), 153 (100), 140 (7), 126 (10). $^1$H-NMR (CDCl$_3$, 500 MHz): δ=7.75 (ddt, J=8.0, 6.3, 1.7 Hz, 1H), 7.20 (dtd, J=9.8, 8.0, 1.7 Hz, 1H), 7.08 (tdd, J=8.2, 4.8, 1.6 Hz, 1H), 5.15 (s, 1H), 3.74 (d, J=7.7 Hz, 4H). $^{13}$C-NMR (CDCl3, 125 MHz): δ=160.1 (s), 151.8 (d, J=13.6 Hz), 150.2 (d, J=14.3 Hz), 149.8 (d, J=13.6 Hz), 148.2 (d, J=14.2 Hz), 125.5 (s), 124.3 (dd, J=6.3, 4.7 Hz), 120.3 (d, J=7.7 Hz), 119.1 (d, J=17.1 Hz), 49.9 (s).

2-(2-Bromo-6-fluorophenyl)-1,4,5,6-tetrahydropyrimidine (11j)

2-Bromo-6-fluorobenzaldehyde (10j) (2.03 g, 10.0 mmol) was subjected to general procedure, using propane-1,3-diamine (916 μl, 815 mg, 11.0 mmol), K$_2$CO$_3$ (4.15 g, 30.0 mmol) and I$_2$ (3.17 g, 12.5 mmol). 2-(2-Bromo-6-fluorophenyl)-1,4,5,6-tetrahydropyrimidine (11j) was received as yellowish solid (2.14 mg, 8.32 mmol, 83%). GC/MS (t$_r$=17.93 min, 70 eV, EI) m/z (%)=258 (22) [M$^+$ ($^{81}$Br)], 256 (27) [M$^+$ ($^{79}$Br)], 239 (26), 237 (27), 201 (20), 200 (30), 177 (100), 121 (29), 18 (27). $^1$H-NMR (CDCl$_3$, 500 MHz): δ=7.31 (d, J=8.1 Hz, 1H), 7.18 (td, J=8.2, 5.8 Hz, 1H), 7.00 (td, J=8.5, 0.9 Hz, 1H), 3.36-3.27 (m, 2H), 1.83-1.75 (m, 1H). $^{13}$C-NMR (CDCl3, 125 MHz): δ=160.1 (d, J=252.3 Hz), 151.1 (s), 131.2 (d, J=8.8 Hz), 128.5 (d, J=3.1 Hz), 126.7 (d, J=20.1 Hz), 122.7 (d, J=3.5 Hz), 115.0 (d, J=22.0 Hz), 41.8 (s), 20.2 (s).

2-(2-Fluoro-4-methylphenyl)-1,4,5,6-tetrahydropyrimidine (11k)

2-Fluoro-4-methylbenzaldehyde (10k) (1.38 g, 10.0 mmol) was subjected to general procedure, using propane-1,3-diamine (916 μl, 815 mg, 11.0 mmol), K$_2$CO$_3$ (4.15 g, 30.0 mmol) and I$_2$ (3.19 g, 12.6 mmol). 2-(2-Fluoro-4-methylphenyl)-1,4,5,6-tetrahydropyrimidine (11k) was received as brown viscous oil (1.93 mg, 10.0 mmol, quant.). GC/MS (t$_r$=17.93 min, 70 eV, EI) m/z (%)=191 [(M–H)$^+$] (100), 173 (38), 136 (68), 116 (20), 89 (18). $^1$H-NMR (CDCl$_3$, 500 MHz): δ=7.48 (t, J=8.0 Hz, 1H), 6.93-6.87 (m, 1H), 6.81 (d, J=12.3 Hz, 1H), 6.36 (s, 1H), 3.38 (dd, J=13.1, 7.3 Hz, 4H), 2.31 (s, 3H), 1.85-1.74 (m, 2H). $^{13}$C-NMR (CDCl3, 125 MHz): δ=159.8 (d, J=248.8 Hz), 153.0 (s), 142.8 (d, J=8.6 Hz), 130.1 (d, J=2.6 Hz), 125.2 (d, J=2.1 Hz), 119.7 (d, J=11.8 Hz), 116.5 (d, J=22.7 Hz), 41.4 (s), 21.2 (s), 20.1 (s).

2-(2-Bromo-5-fluorophenyl)-1,4,5,6-tetrahydropyrimidine (11l)

2-Bromo-5-fluorobenzaldehyde (10l) (2.04 g, 10.0 mmol) was subjected to general procedure, using propane-1,3-diamine (916 μl, 815 mg, 11.0 mmol), K$_2$CO$_3$ (4.15 g, 30.0 mmol) and I$_2$ (3.18 g, 12.5 mmol). 2-(2-Bromo-5- fluorophenyl)-1,4,5,6-tetrahydropyrimidine (11l) was received as colorless solid (1.93 mg, 7.49 mmol, 75%). GC/MS (t$_r$=14.63 min, 70 eV, EI) m/z (%)=258 (43) [M$^+$ ($^{81}$Br)], 257 (79) [M$^+$–H ($^{81}$Br)], 256 (25) [M$^+$ ($^{79}$Br)], 255 (78) [M$^+$–H ($^{79}$Br)], 202 (36), 200 (36), 177 (100), 121 (55), 120 (31). $^1$H-NMR (CDCl$_3$, 500 MHz): δ=7.71 (td, J=8.8, 6.6 Hz, 1H), 6.87-6.81 (m, 1H), 6.74 (ddd, J=11.3, 8.7, 2.5 Hz, 1H), 5.74 (s, 1H), 3.49-3.33 (m, 4H), 1.98-1.58 (m, 2H). $^{13}$C-NMR (CDCl3, 125 MHz): δ=161.8 (d, J=248.3 Hz), 154.6 (s), 140.7 (d, J=7.5 Hz), 134.3 (d, J=7.9 Hz), 117.6 (d, J=23.9 Hz), 117.4 (d, J=22.5 Hz), 115.1 (d, J=3.0 Hz), 42.2 (s), 20.6 (s).

2-(2-Fluoro-6-methylphenyl)-1,4,5,6-tetrahydropyrimidine (11m)

2-Fluoro-6-methylbenzaldehyde (10m) (1.01 g, 7.30 mmol) was subjected to general procedure, using propane-1,3-diamine (663 μl, 590 mg, 7.75 mmol), K$_2$CO$_3$ (2.99 g, 21.7 mmol) and I$_2$ (2.30 g, 9.06 mmol). 2-(2-Fluoro-4-methylphenyl)-1,4,5,6-tetrahydropyrimidine (11m) was received as yellowish solid (1.13 mg, 5.87 mmol, 80%). GC/MS (t$_r$=15.23 min, 70 eV, EI) m/z (%)=192 [M$^+$] (100), 177 (45), 173 (19), 135 (46), 116 (15), 89 (12). $^1$H-NMR (CDCl$_3$, 300 MHz): δ=7.25 (s, J=3.7 Hz, 1H), 7.17 (td, J=8.0, 5.9 Hz, 1H), 6.90 (d, J=7.6 Hz, 1H), 6.82 (t, J=8.8 Hz, 1H), 3.12-3.02 (m, 4H), 2.17 (s, 3H), 1.71-1.60 (m, 2H). $^{13}$C-NMR (CDCl3, 75 MHz): δ=159.7 (d, J=247.3 Hz), 152.4 (s), 138.7 (d, J=2.4 Hz), 130.3 (d, J=8.8 Hz), 125.8 (d, J=2.8 Hz), 123.9 (d, J=16.5 Hz), 112.8 (d, J=21.6 Hz), 40.8 (s), 19.9 (s), 18.6 (d, J=2.1 Hz).

2-(2-Fluoro-5-methylphenyl)-4,5-dihydro-1H-imidazole (11n)

2-Fluoro-5-methylbenzaldehyde (10n) (1.38 g, 10.0 mmol) was subjected to general procedure, using ethane-1,2-diamine (734 μL, 660 mg, 11.0 mmol), K$_2$CO$_3$ (4.15 g, 30.1 mmol) and I$_2$ (3.20 g, 12.6 mmol). 2-(2-Fluoro-5 methylphenyl)-4,5-dihydro-1H-imidazole (11n) was received as yellowish solid (1.71 g, 9.57 mmol, 96%).

2.2 Cyclization Using Carbon Disulfide

General Procedure

To a mixture of 10 (1 eq.) and NaH (2 eq.) in DMF (3.3 ml/mmol) was added CS$_2$ (2 eq.) under nitrogen atmosphere. After stirring at 80° C. for 16 h the mixture was concentrated in vacuo. The product was purified via chromatography.

3,4-Dihydrobenzo[e]pyrimido[1,2-c][1,3]thiazine-6(2H)-thione(12a)

2-(2-Bromophenyl)-1,4,5,6-tetrahydropyrimidine (11a) (930 mg, 3.89 mmol) was dissolved in 10 ml dry DMF, NaH (311 mg, 7.78 mmol, 60% suspension in oil) and CS$_2$ (470 μl, 7.78 mmol) were added and the mixture stirred for 15 h at rt. Afterwards 800 μl MeOH was added and the solvent was evaporated. Purification via silica column chromatography (hexane:EtOAc 8:2; Rr: 0.4) gave the product as a bright yellow solid (500 mg, 55%). $^1$H NMR (300 MHz, CDCl$_3$) δ 8.21 (dd, J=8.0, 1.3 Hz, 1H, Ar), 7.44-7.36 (m, 1H, Ar), 7.33-7.26 (m, 1H, Ar), 7.10-6.94 (m, 1H, Ar), 4.56-4.25 (m, 2H, CH$_2$), 3.75 (t, J=5.6 Hz, 2H, CH$_2$), 2.22-1.86 (m, 2H, CH$_2$). $^{13}$C NMR (75 MHz, CDCl$_3$) δ 189.78, 144.43, 131.93, 131.24, 128.95, 127.60, 126.31, 121.66, 48.76, 45.51, 21.62.

2H-Benzo[e]imidazo[1,2-c][1,3]thiazine-5(3H)-thione (12b)

2-(2-bromophenyl)-4,5-dihydro-1H-imidazole (11b) (261 mg, 1.00 mmol) was subjected to general procedure for cyclization using NaH (60%, 80.0 mg, 2.00 mmol) and carbon disulfide (120 μl, 151 mg, 1.99 mmol). 2H-benzo[e]imidazo[1,2-c][1,3]thiazine-5(3H)-thione (4a) was received as yellow crystals (156 mg, 612 μmol, 61%). GC/MS (t$_r$=23.03 min, 70 eV, EI) m/z (%)=220 [M$^+$] (100), 187 (30), 161 (31), 135 (27), 86 (37). $^1$H-NMR (CDCl$_3$, 500 MHz): δ=8.17 (d, J=7.9 Hz, 1H), 7.47 (td, J=8.0, 1.2 Hz, 1H), 7.38-7.29 (m, 1H), 7.11 (d, J=8.0 Hz, 1H), 4.46-4.33 (m, 2H), 4.21-4.11 (m, 2H). $^{13}$C-NMR (CDCl$_3$, 125 MHz): δ=183.3, 151.6, 134.9, 132.7, 129.2, 127.8, 122.4, 120.6, 52.5, 52.1.

9-Chloro-2H-benzo[e]imidazo[1,2-c][1,3]thiazine-5(3H)-thione (12c)

2-(2-Bromo-5-chlorophenyl)-4,5-dihydro-1H-imidazole (11c) (520 mg, 2.00 mmol) was subjected to general procedure for cyclization using NaH (60%, 82.1 mg, 2.05 mmol) and carbon disulfide (120 μl, 151 mg, 1.99 mmol). 9-Chloro-2H-benzo[e]imidazo[1,2-c][1,3]thiazine-5(3H)-thione (4b) was received as yellow crystals (360 mg, 1.41 mmol, 71%). GC/MS (t$_r$=24.61 min, 70 eV, EI) m/z (%)=254 [M$^+$] (100), 221 (36), 195 (34), 169 (22), 86 (64). $^1$H-NMR (CDCl$_3$, 500 MHz): δ=8.13 (d, J=2.3 Hz, 1H), 7.42 (dd, J=8.5, 2.3 Hz, 1H), 7.04 (d, J=8.5 Hz, 1H), 4.48-4.29 (m, 2H), 4.22-4.07 (m, 2H). $^{13}$C-NMR (CDCl3, 125 MHz): δ=182.4, 150.7, 133.8, 133.2, 132.9, 128.9, 123.8, 122.1, 52.8, 52.3.

9-(Dimethylamino)-3,4-dihydrobenzo[e]pyrimido[1,2-c][1,3]thiazine-6(2H)-thione (12d)

2-(2-Bromo-4-dimethylaminophenyl)-1,4,5,6-tetrahydropyrimidine (11d) (283 mg, 1.00 mmol) was subjected to general procedure for cyclization using NaH (60%, 87.0 mg, 2.18 mmol) and carbon disulfide (120 μl, 151 mg, 1.99 mmol). 9-(dimethylamino)-3,4-dihydrobenzo[e]pyrimido[1,2-c][1,3]thiazine-6(2H)-thione (5c) was received as yellow crystals (159 mg, 574 μmol, 57%). GC/MS (t$_r$=28.95 min, 70 eV, EI) m/z (%)=277 [M$^+$](100), 244 (14), 219 (66), 191 (27), 177 (37).

10-Chloro-3,4-dihydrobenzo[e]pyrimido[1,2-c][1,3]thiazine-6(2H)-thione (12e)

2-(2-Bromo-5-chlorophenyl)-1,4,5,6-tetrahydropyrimidine (11e) (274 mg, 1.00 mmol) was subjected to general procedure for cyclization using NaH (60%, 80.9 mg, 2.00 mmol) and carbon disulfide (121 μl, 152 mg, 2.00 mmol). 10-Chloro-3,4-dihydrobenzo[e]pyrimido[1,2-c][1,3]thiazine-6(2H)-thione (5b) was received as yellow crystals (168 mg, 626 μmol, 63%). GC/MS (t$_r$=25.49 min, 70 eV, EI) m/z (%)=268 [M$^+$] (100), 235 (14), 210 (62), 169 (22), 133 (16), 100 (28), 72 (65). $^1$H-NMR (CDCl$_3$, 500 MHz): δ=8.21 (d, J=2.3 Hz, 1H), 7.36 (dd, J=8.4, 2.3 Hz, 1H), 6.96 (d, J=8.4 Hz, 1H), 4.50-4.31 (m, 2H), 3.75 (t, J=5.6 Hz, 2H), 2.03 (ddd, J=11.4, 7.8, 6.0 Hz, 2H). $^{13}$C-NMR (CDCl3, 125 MHz): δ=δ 189.1, 143.3, 133.6, 131.4, 130.2, 128.8, 127.8, 123.0, 48.7, 45.6, 21.6.

9-Fluoro-3,4-dihydrobenzo[e]pyrimido[1,2-c][1,3]thiazine-6(2H)-thione (12f)

2-(2,4-Difluorophenyl)-1,4,5,6-tetrahydropyrimidine (11f) (783 mg, 3.99 mmol) was subjected to general procedure for cyclization using NaH (60%, 195 mg, 8.14 mmol) and carbon disulfide (483 µl, 609 mg, 8.00 mmol). 9-Fluoro-3,4-dihydrobenzo[e]pyrimido[1,2-c][1,3]thiazine-6(2H)-thione (5d) was received as yellow crystals (656 mg, 2.60 mmol, 65%). GC/MS ($t_r$=23.17 min, 70 eV, EI) m/z (%)=252 (100) [M$^+$], 194 (50), 192 (17), 166 (16), 99 (18), 72 (52), 41 (22). $^1$H-NMR (CDCl$_3$, 500 MHz): δ=8.20 (dd, J=9.0, 5.6 Hz, 1H), 6.96 (td, J=8.6, 2.5 Hz, 1H), 6.70 (dd, J=7.9, 2.5 Hz, 1H), 4.45-4.34 (m, 2H), 3.72 (t, J=5.6 Hz, 2H), 2.02 (dt, J=11.9, 5.9 Hz, 2H). $^{13}$C-NMR (CDCl3, 125 MHz): δ=188.9 (s), 164.0 (d, J=255.4 Hz), 143.5 (s), 134.1 (d, J=8.7 Hz), 131.8 (d, J=8.9 Hz), 122.8 (s), 115.2 (d, J=22.0 Hz), 108.1 (d, J=24.7 Hz), 48.8 (s), 45.5 (s), 21.6 (s).

9-Bromo-3,4-dihydrobenzo[e]pyrimido[1,2-c][1,3]
thiazine-6(2H)-thione (12g)

2-(4-Bromo-2-fluorophenyl)-1,4,5,6-tetrahydropyrimidine (11g) (1.02 g, 3.96 mmol) was subjected to general procedure for cyclization using NaH (60%, 322 mg, 8.05 mmol) and carbon disulfide (480 µl, 605 mg, 8.05 mmol). 9-Bromo-3,4-dihydrobenzo[e]pyrimido[1,2-c][1,3]thiazine-6(2H)-thione (5e) was received as yellow crystals (578 mg, 1.84 mmol, 47%). GC/MS ($t_r$=26.19 min, 70 eV, EI) m/z (%)=314 (100) [M$^+$ ($^{81}$Br)], 312 (94) [M$^+$ ($^{79}$Br)], 256 (67), 254 (76), 113 (26), 72 (80), 41 (32). $^1$H-NMR (CDCl$_3$, 500 MHz): δ=8.05 (d, J=8.7 Hz, 1H), 7.38 (dd, J=8.7, 1.9 Hz, 1H), 7.15 (d, J=1.9 Hz, 1H), 4.47-4.35 (m, 2H), 3.72 (t, J=5.6 Hz, 2H), 2.02 (dt, J=11.6, 5.9 Hz, 2H). $^{13}$C-NMR (CDCl$_3$, 125 MHz): δ=188.9, 143.7, 133.8, 130.7, 126.0, 125.4, 124.07, 48.7, 45.7, 21.6.

8-Fluoro-3,4-dihydrobenzo[e]pyrimido[1,2-c][1,3]
thiazine-6(2H)-thione (12 h)

2-(2,3-Difluorophenyl)-1,4,5,6-tetrahydropyrimidine (11h) (788 mg, 4.01 mmol) was subjected to general procedure for cyclization using NaH (60%, 320 mg, 8.00 mmol) and carbon disulfide (490 µl, 617 mg, 8.11 mmol). 8-Fluoro-3,4-dihydrobenzo[e]pyrimido[1,2-c][1,3]thiazine-6(2H)-thione (5d) was received as yellow crystals (595 mg, 2.36 mmol, 59%). GC/MS ($t_r$=23.53 min, 70 eV, EI) m/z (%)=252 (100) [M$^+$], 219 (10), 194 (46), 153 (17), 72 (48), 41 (21). $^1$H-NMR (CDCl$_3$, 500 MHz): δ=8.00 (d, J=8.1 Hz, 1H), 7.25 (ddd, J=13.8, 7.9, 5.7 Hz, 1H), 7.16-7.09 (m, 1H), 4.46-4.38 (m, 2H), 3.75 (t, J=5.6 Hz, 2H), 2.08-1.99 (m, 2H). $^{13}$C-NMR (CDCl3, 125 MHz): δ=188.2 (s), 153.8 (d, J=245.2 Hz), 143.3 (d, J=3.4 Hz), 128.0 (s, J=2.1 Hz), 127.9 (d, J=7.6 Hz), 124.4 (d, J=2.9 Hz), 120.7 (d, J=20.1 Hz), 117.0 (d, J=19.5 Hz), 48.8 (s), 45.6 (s), 21.6 (s).

7-Fluoro-2H-benzo[e]imidazo[1,2-c][1,3]thiazine-5
(3H)-thione (12i)

2-(2,3-Difluorophenyl)-4,5-dihydro-1H-imidazole (11i) (728 mg, 4.00 mmol) was subjected to general procedure for cyclization using NaH (60%, 321 mg, 8.02 mmol) and carbon disulfide (490 µl, 617 mg, 8.11 mmol). 7-Fluoro-2H-benzo[e]imidazo[1,2-c][1,3]thiazine-5(3H)-thione (12i) was received as yellow solid (727 mg, 3.05 mmol, 76%). GC/MS ($t_r$=24.61 min, 70 eV, EI) m/z (%)=254 [M$^+$] (100), 221 (36), 195 (34), 169 (22), 86 (64). $^1$H-NMR (CDCl$_3$, 500 MHz): δ=7.94 (d, J=7.9 Hz, 1H), 7.35-7.24 (m, 1H), 7.22-7.15 (m, 1H), 4.39-4.33 (m, 2H), 4.16-4.11 (m, 2H). $^{13}$C-NMR (CDCl3, 125 MHz): δ=181.4 (s), 154.4 (d, J=246.3 Hz), 150.7 (s), 128.4 (d, J=7.6 Hz), 124.7 (d, J=3.1 Hz), 123.4 (d, J=19.7 Hz), 122.4 (s), 118.5 (d, J=19.8 Hz), 52.9 (s), 52.3 (s).

11-Bromo-3,4-dihydrobenzo[e]pyrimido[1,2-c][1,3]
thiazine-6(2H)-thione (12j)

2-(2-Bromo-6-fluorophenyl)-1,4,5,6-tetrahydropyrimidine (11j) (1.03 g, 4.00 mmol) was subjected to general procedure for cyclization using NaH (60%, 320 mg, 8.00 mmol) and carbon disulfide (490 µl, 617 mg, 8.11 mmol). 11-Bromo-3,4-dihydrobenzo[e]pyrimido[1,2-c][1,3]thiazine-6(2l)-thione (12j) was received as yellow crystals (210 mg, 670 µmol, 17%). GC/MS ($t_r$=25.54 min, 70 eV, EI) m/z (%)=314 (80) [M$^+$ ($^{79}$Br)], 312 (76) [M$^+$ ($^{79}$Br)], 255 (64), 253 (73), 133 (30), 100 (37), 72 (100), 41 (42). $^1$H-NMR (CDCl$_3$, 500 MHz): δ=7.63 (dd, J=8.0, 0.9 Hz, 1H), 7.21 (t, J=7.9 Hz, 1H), 7.07 (dd, J=7.9, 0.9 Hz, 1H), 4.39-4.28 (m, 2H), 3.84 (t, J=5.7 Hz, 2H), 2.16-2.06 (m, 2H). $^{13}$C-NMR (CDCl3, 125 MHz): δ=187.9, 144.6, 134.9, 134.3, 131.2, 125.9, 122.8, 121.9, 48.3, 45.9, 23.4.

9-Methyl-3,4-dihydrobenzo[e]pyrimido[1,2-c][1,3]
thiazine-6(2H)-thione (12k)

2-(2-Fluoro-4-methylphenyl)-1,4,5,6-tetrahydropyrimidine (11k) (767 mg, 3.99 mmol) was subjected to general procedure for cyclization using NaH (60%, 322 mg, 8.06 mmol) and carbon disulfide (490 µl, 617 mg, 8.11 mmol). 9-Methyl-3,4-dihydrobenzo[e]pyrimido[1,2-c][1,3]thiazine-6(2H)-thione (12k) was received as yellow crystals (323 mg, 1.30 mmol, 33%). $^1$H-NMR (CDCl$_3$, 500 MHz): δ=8.14 (d, J=8.0 Hz, 1H), 7.12 (d, J=8.1 Hz, 1H), 6.83 (s, 1H), 4.49-4.41 (m, 2H), 3.75 (t, J=5.6 Hz, 2H), 2.36 (s, 3H), 2.04 (dt, J=11.8, 5.9 Hz, 2H). $^{13}$C-NMR (CDCl3, 125 MHz): δ=190.1, 144.9, 142.3, 132.0, 129.1, 129.0, 123.6, 121.8, 48.9, 45.4, 21.6, 21.4.

10-Fluoro-3,4-dihydrobenzo[e]pyrimido[1,2-c][1,3]
thiazine-6(2H)-thione (12l)

2-(2-Bromo-5-fluorophenyl)-1,4,5,6-tetrahydropyrimidine (11l) (1.03 g, 4.00 mmol) was subjected to general procedure for cyclization using NaH (60%, 320 mg, 8.00 mmol) and carbon disulfide (490 µl, 617 mg, 8.11 mmol). 10-Fluoro-3,4-dihydrobenzo[e]pyrimido[1,2-c][1,3]thiazine-6(2H)-thione (12l) was received as yellow solid (482 mg, 1.90 mmol, 48%). GC/MS ($t_r$=23.17 min, 70 eV, EI) m/z (%)=23.43 min, 70 eV, EI) m/z (%)=252 (100) [M$^+$], 194 (48), 100 (20), 72 (49). $^1$H-NMR (CDCl$_3$, 500 MHz): δ=7.92 (dd, J=10.1, 2.8 Hz, 1H), 7.16-7.10 (m, 1H), 6.98 (dd, J=8.7, 5.0 Hz, 1H), 4.47-4.39 (m, 2H), 3.74 (t, J=5.6 Hz, 2H), 2.03 (dt, J=12.2, 5.9 Hz, 2H). $^{13}$C-NMR (CDCl3, 125 MHz): δ=189.3 (s), 161.9 (d, J=247.1 Hz), 143.4 (s), 128.5 (d, J=8.1 Hz), 127.4 (s), 123.6 (d, J=7.8 Hz), 119.2 (d, J=23.4 Hz), 115.6 (d, J=25.2 Hz), 48.6 (s), 45.6 (s), 21.6 (s).

11-Methyl-3,4-dihydrobenzo[e]pyrimido[1,2-c][1,3]
thiazine-6(2H)-thione (12m)

2-(2-Fluoro-6-methylphenyl)-1,4,5,6-tetrahydropyrimidine (11m) (716 mg, 3.72 mmol) was subjected to general procedure for cyclization using NaH (60%, 325 mg, 8.13 mmol) and carbon disulfide (480 µl, 605 mg, 7.94 mmol). 11-Methyl-3,4-dihydrobenzo[e]pyrimido[1,2-c][1,3]thiazine-6(2H)-thione (12m) was received as yellow solid (528 mg, 2.13 mmol, 57%). 12m was immediately reacted with bromine cyanide to yield 13m (see below).

2.3 Cyclization Using Bromine Cyanide

General Procedure

The thiazinethione 11 (1 eq.) was suspended in 0.1 M NaOH (20 ml/mmol, MeOH:H$_2$O=9:1) and the mixture was stirred under reflux for 16 h. The solvent was removed in vacuo and the residue was dried azeotrope with MeOH (3×20 ml/mmol) and CHCl$_3$ (2×20 ml/mmol). The solid was suspended under Argon atmosphere in dry EtOH (4 ml/mmol) and BrCN (2 eq.) was added. The mixture was stirred under reflux for 3 h, 2 M NaOH (4 ml/mmol) was added and the solution was extracted with CHCl$_3$ (2×20 mL/mmol). The combined organic layers were dried (Na$_2$SO$_4$) and the solvent was removed in vacuo. The crude product was purified by column chromatography (AlO$_2$—N).

3,4-dihydrobenzo[e]pyrimido[1,2-c][1,3]thiazin-6 (2H)-imine (13a)

3,4-Dihydrobenzo[e]pyrimido[1,2-c][1,3]thiazine-6(2H)-thione (12a) (450 mg, 1.92 mmol) was suspended in 36 ml MeOH and 4 ml 0.1 M NaOH and stirred under reflux for 9 h and 14 h at rt. Afterwards the solvent was evaporated and coevaporated (2×20 ml MeOH, 2×20 ml CHCl3). The residue was suspended in dry EtOH (8 ml), BrCN (406 mg, 3.84 mmol) was added and the mixture was stirred under reflux. After 2.5 h the suspension was cooled to 0° C., 2 M NaOH (2 mL) was added and the whole was extracted with CHCl3 (3×20 ml). The combined organics were washed with brine, dried over Na$_2$SO$_4$, filtered and concentrated in vacuo. The crude product was purified by column chromatography (Al2O3, hexane-EtOAc 9:1, Rf:0.25) to obtain 40 mg (10%) of the desired compound and 210 mg of the starting material. $^1$H NMR (300 MHz, CDCl3) δ 8.21 (dd, J=7.9, 1.6 Hz, 1H, Ar), 7.46-7.10 (m, 3H, NH, 2Ar), 7.10-6.95 (m, 1H, Ar), 4.13-3.95 (m, 2H, CH2), 3.68 (t, 2H, CH2), 2.08-1.87 (m, 2H, CH2). $^{13}$C NMR (75 MHz, CDCl3) δ 153.51, 146.72, 130.67, 128.96, 126.93, 126.39, 123.67, 45.06, 43.94, 21.17.

2H-Benzo[e]imidazo[1,2-c][1,3]thiazin-5(3H)-imine (13b) (also named 6a)

12b (110 mg, 500 μmol) was subjected to the general procedure using BrCN (120 mg, 1.13 mmol). After purification 2H-benzo[e]imidazo[1,2-c][1,3]thiazin-5(3H)-imine (13b) (21.2 mg, 104 μmol, 21%) was obtained as a colorless solid. LC/MS (t$_r$=1.145 min, ESI) M+H$^+$$_{(measured)}$=204.1, M+H$^+$$_{(calculated)}$=204.059. $^1$H-NMR (CDCl$_3$, 500 MHz): δ=8.19 (dd, J=8.0, 1.2 Hz, 1H), 7.42-7.34 (m, 1H), 7.28-7.20 (m, 1H), 7.11 (dd, J=8.0, 0.7 Hz, 1H), 4.10 (s, 4H). $^{13}$C-NMR (CDCl$_3$, 126 MHz): δ=154.2, 132.1, 129.2, 126.6, 123.9, 121.1, 53.2, 47.5.

9-Chloro-2H-benzo[e]imidazo[1,2-c][1,3]thiazin-5 (3H)-imine (13c) (also named 6b)

12c (128 mg, 502 μmol) was subjected to the general procedure using BrCN (139 mg, 1.31 mmol). After purification 9-Chloro-2H-benzo[e]imidazo[1,2-c][1,3]thiazin-5 (3H)-imine (13c) (34.7 mg, 146 μmol, 29%) was obtained as a colorless solid. LC/MS (t$_r$=5.935 min, ESI) M+H$^+$$_{(measured)}$=238.0, M+H$^+$$_{(calculated)}$=238.020. $^1$H-NMR (CDCl$_3$, 500 MHz): δ=8.15 (d, J=2.2 Hz, 1H), 7.36 (dd, J=8.5, 2.3 Hz, 1H), 7.06 (d, J=8.5 Hz, 1H), 4.09 (s, 4H). $^{13}$C-NMR (CDCl$_3$, 126 MHz): δ=152.9, 150.7, 133.0, 132.5, 130.2, 128.9, 125.3, 122.0, 53.1, 47.7, 29.7.

6-Imino-N,N-dimethyl-2,3,4,6-tetrahydrobenzo[e] pyrimido[1,2-c][1,3]thiazin-9-imine (13d) (also named 7c)

12d (84.3 mg, 304 μmol) was subjected to the general procedure using BrCN (95.0 mg, 897 μmol). After purification 6-Imino-2H-benzo[e]imidazo[1,2-c][1,3]thiazin-5 (3H)-imine (13d) (32.5 mg, 125 μmol, 41%) was obtained as a colorless solid. LC/MS (t$_r$=8.143 min, ESI) M+H$^+$$_{(measured)}$=261.1, M+H$^+$$_{(calculated)}$=261.117. $^1$H-NMR (CDCl$_3$, 500 MHz): δ=8.10-8.03 (m, 1H), 6.58-6.52 (m, 1H), 6.17 (d, J=2.6 Hz, 1H), 4.04-3.96 (m, 2H), 3.64 (t, J=5.6 Hz, 2H), 2.97 (s, 6H), 2.00-1.91 (m, 2H). $^{13}$C-NMR (CDCl$_3$, 126 MHz): δ=$^{13}$C NMR (126 MHz, CDCl$_3$) δ 154.4, 151.6, 147.1, 130.1, 130.1, 114.4, 110.9, 104.6, 44.8, 44.0, 40.1, 21.3.

10-Chloro-3,4-dihydrobenzo[e]pyrimido[1,2-c][1,3] thiazin-6(2H)-imine (13e) (also named 7b)

12e (134 mg, 500 μmol) was subjected to the general procedure using BrCN (123 mg, 1.17 mmol). After purification 10-Chloro-3,4-dihydrobenzo[e]pyrimido[1,2-c][1,3] thiazin-6(2H)-imine (13e) (35.6 mg, 141 μmol, 28%) was obtained as a colorless solid. LC/MS (t$_r$=8.143 min, ESI) M+H$^+$$_{(measured)}$=252.1, M+H$^+$$_{(calculated)}$=252.036. $^1$H-NMR (500 MHz, CDCl$_3$) δ=8.23 (d, J=2.3 Hz, 1H), 7.35-7.13 (m, 2H), 6.95 (d, J=8.4 Hz, 1H), 4.05-3.94 (m, 2H), 3.68 (t, J=5.6 Hz, 2H), 2.01-1.89 (m, 2H). $^{13}$C-NM (126 MHz, CDCl$_3$) δ 152.7, 145.6, 132.5, 130.8, 128.87, 128.3, 127.3, 124.9, 45.1, 43.9, 21.1.

9-Fluoro-3,4-dihydrobenzo[e]pyrimido[1,2-c][1,3] thiazin-6(2H)-imine (13f) (also named 7d)

12f (252 mg, 998 μmol) was subjected to the general procedure using BrCN (287 mg, 2.71 mmol). After purification 9-Fluoro-2H-benzo[e]imidazo[1,2-c][1,3]thiazin-5 (3H)-imine (13f) (82.4 mg, 350 μmol, 35%) was obtained as a colorless solid. LC/MS (t$_r$=8.143 min, ESI) M+H$^+$$_{(measured)}$=261.1, M+H$^+$$_{(calculated)}$=235.058. $^1$H-NMR (CDCl$_3$, 500 MHz): δ=8.21 (dd, J=9.0, 5.8 Hz, 1H), 7.23 (s, J=15.6 Hz, 1H), 6.88 (ddd, J=9.0, 8.1, 2.6 Hz, 1H), 6.72 (dd, J=8.2, 2.5 Hz, 1H), 3.98 (t, J=6.1 Hz, 2H), 3.64 (t, J=5.6 Hz, 2H), 1.94 (td, J=11.4, 6.0 Hz, 2H). $^{13}$C-NMR (CDCl$_3$, 126 MHz): δ=163.7 (d, J=253.6 Hz), 152.6 (s), 145. (s), 131.6 (d, J=8.9 Hz), 131.0 (d, J=9.1 Hz), 123.1 (s), 114.0 (d, J=21.7 Hz), 110.1 (d, J=24.9 Hz), 44.9 (s), 43.9 (s), 21.1 (s).

9-Bromo-3,4-dihydrobenzo[e]pyrimido[1,2-c][1,3] thiazin-6(2H)-imine (13g) (also named 7e)

12g (313 mg, 1.00 mmol) was subjected to the general procedure using BrCN (226 mg, 2.13 mmol). After purification 9-Bromo-2H-benzo[e]imidazo[1,2-c][1,3]thiazin-5 (3H)-imine (13g) (89.9 mg, 304 μmol, 30%) was obtained as a colorless solid. LC/MS (t$_r$=1.124 min, ESI) M+H$^+$$_{(measured)}$=296.0, M+H$^+$$_{(calculated)}$=295.985.

8-Fluoro-3,4-dihydrobenzo[e]pyrimido[1,2-c][1,3] thiazin-6(2H)-imine (13 h) (also named 7f)

12 h (252 mg, 998 μmol) was subjected to the general procedure using BrCN (211 mg, 1.99 mmol). After purification 8-Fluoro-3,4-dihydrobenzo[e]pyrimido[1,2-c][1,3]thiazin-6(2H)-imine (13 h) (123 mg, 524 µmol, 53%) was obtained as a colorless solid. LC/MS ($t_r$=1.127 min, ESI) M+H$^+_{(measured)}$=236.1, M+H$^+_{(calculated)}$=236.065. $^1$H-NMR (CDCl$_3$, 500 MHz): δ=8.05-7.99 (m, 1H), 7.34 (s, 1H), 7.17 (td, J=8.1, 5.7 Hz, 1H), 7.08 (td, J=8.6, 1.2 Hz, 1H), 4.01 (t, J=6.0 Hz, 2H), 3.67 (t, J=5.6 Hz, 2H), 2.00-1.92 (m, 2H). $^{13}$C-NMR (CDCl$_3$, 126 MHz): δ=155.7 (d, J=243.5 Hz), 151.8 (s), 145.8 (d, J=3.1 Hz), 128.5 (s), 126.5 (d, J=7.6 Hz), 124.4 (d, J=2.7 Hz), 116.5 (d, J=19.7 Hz), 45.0 (s), 44.0 (s), 21.0 (s).

7-Fluoro-2H-benzo[e]imidazo[1,2-c][1,3]thiazin-5(3H)-imine (13i)

12i (238 mg, 997 µmol) was subjected to the general procedure using BrCN (232 mg, 2.19 mmol). After purification 7-Fluoro-2H-benzo[e]imidazo[1,2-c][1,3]thiazin-5(3H)-imine (13i) (45.5 mg, 206 µmol, 21%) was obtained as a colorless solid. LC/MS ($t_r$=5.935 min, ESI) M+H$^+_{(measured)}$=238.0, M+H$^+_{(calculated)}$=238.020. $^1$H-NMR (CDCl$_3$, 500 MHz): δ=8.15 (d, J=2.2 Hz, 1H), 7.36 (dd, J=8.5, 2.3 Hz, 1H), 7.06 (d, J=8.5 Hz, 1H), 4.09 (s, 4H). $^{13}$C-NMR (CDCl$_3$, 126 MHz): δ=152.9, 150.7, 133.0, 132.5, 130.2, 128.9, 125.3, 122.0, 53.1, 47.7, 29.7.

11-Bromo-3,4-dihydrobenzo[e]pyrimido[1,2-c][1,3]thiazin-6(2H)-imine (13j)

12j (156 mg, 498 µmol) was subjected to the general procedure using BrCN (106 mg, 997 mmol). After purification 11-Bromo-3,4-dihydrobenzo[e]pyrimido[1,2-c][1,3]thiazin-6(2H)-imine (13j) (52.3 mg, 177 µmol, 35%) was obtained as a yellowish solid. LC/MS ($t_r$=5. min, ESI) M+H$^+_{(measured)}$=0.1, M+H$^+_{(calculated)}$=232.090.

9-Methyl-3,4-dihydrobenzo[e]pyrimido[1,2-c][1,3]thiazin-6(2H)-imine (13k)

12k (248 mg, 499 µmol) was subjected to the general procedure using BrCN (293 mg, 2.76 mmol). After purification 9-Methyl-3,4-dihydrobenzo[e]pyrimido[1,2-c][1,3]thiazin-6(2H)-imine (13k) (123 mg, 530 µmol, 28%) was obtained as a colorless solid. LC/MS ($t_r$=5.337 min, ESI) M+H$^+_{(measured)}$=232.1, M+H$^+_{(calculated)}$=232.090. $^1$H-NMR (300 MHz, CDCl$_3$) δ=8.09 (d, J=8.2 Hz, 1H), 7.00 (dd, J=8.3, 1.0 Hz, 1H), 6.81 (s, 1H), 4.04-3.94 (m, 2H), 3.65 (t, J=5.6 Hz, 2H), 2.30 (s, 3H), 1.94 (td, J=11.3, 6.0 Hz, 2H). $^{13}$C-NMR (75 MHz, CDCl$_3$) δ=153.7, 146.7, 141.2, 128.9, 128.7, 127.6, 124.1, 123.7, 44.9, 43.9, 21.2, 21.1.

10-Fluoro-3,4-dihydrobenzo[e]pyrimido[1,2-c][1,3]thiazin-6(2H)-imine (13l)

12l (241 mg, 954 µmol) was subjected to the general procedure using BrCN (212 mg, 2.00 mmol). After purification 10-Fluoro-3,4-dihydrobenzo[e]pyrimido[1,2-c][1,3]thiazin-6(2H)-imine (13l) (73.3 mg, 312 µmol, 33%) was obtained as a colorless solid. LC/MS ($t_r$=1.105 min, ESI) M+H$^+_{(measured)}$=236.1, M+H$^+_{(calculated)}$=236.065. $^1$H-NMR (500 MHz, CDCl$_3$) δ=7.27 (td, J=8.1, 4.8 Hz, 1H), 6.98 (ddd, J=11.1, 8.3, 0.9 Hz, 1H), 6.89 (d, J=7.9 Hz, 1H), 3.93 (t, J=6.4 Hz, 2H), 3.72 (t, J=5.4 Hz, 2H), 1.98 (td, J=11.5, 6.1 Hz, 2H). $^{13}$C-NMR (125 MHz, CDCl$_3$) δ=160.6 (d, J=261.6 Hz), 152.6 (s), 144.9 (d, J=9.2 Hz), 131.6 (s), 131.2 (d, J=9.9 Hz), 120.1 (d, J=4.0 Hz), 117.4 (d, J=9.1 Hz), 115.4 (d, J=24.0 Hz), 45.5 (s), 44.1 (s), 21.8 (s).

11-Methyl-3,4-dihydrobenzo[e]pyrimido[1,2-c][1,3]thiazin-6(2H)-imine (13m)

12m (232 mg, 933 µmol) was subjected to the general procedure using BrCN (251 mg, 2.37 mmol). After purification 11-Methyl-3,4-dihydrobenzo[e]pyrimido[1,2-c][1,3]thiazin-6(2H)-imine (13m) (74.2 mg, 321 µmol, 34%) was obtained as a colorless solid. LC/MS ($t_r$=6.153 min, ESI) M+H$^+_{(measured)}$=232.1, M+H$^+_{(calculated)}$=236.090. $^1$H-NMR (500 MHz, CDCl$_3$) δ=7.17 (t, J=7.7 Hz, 1H), 7.13-7.09 (m, 1H), 6.97 (dd, J=7.7, 0.4 Hz, 1H), 3.89 (t, J=6.5 Hz, 2H), 3.70-3.64 (m, 2H), 2.58 (s, 3H), 1.99-1.91 (m, 2H). $^{13}$C-NMR (125 MHz, CDCl$_3$) δ=153.9, 148.8, 139.3, 130.6, 129.8, 129.4, 128.1, 122.6, 45.3, 44.2, 23.0, 22.7.

Example 3 Inhibition of Histonedeacetylase Activity

For HDAC 1, 2, 3 and 6:

The activity of HDAC1 was determined by a colorimetric assay as described by Wegener et al (2003). 1 nM of HDAC1 was incubated with increasing concentrations of the respective compound for 30 minutes at 30° C. The reaction was initiated by addition of 50 µM of the substrate Boc-Lys(Ac)-AMC. After an incubation of 60 minutes the reaction was stopped by addition of 20 µM SAHA and the deacetylated substrate was converted into a fluorescent product by the addition of trypsin.

For HDAC 4, 5, 7 and 8:

The activity of HDAC4 was determined by a colorimetric assay as described by Wegener et al. (2003). 1 nM of HDAC4 was incubated with increasing concentrations of the respective compound for 30 minutes at 30° C. The reaction was initiated by addition of 20 µM of the substrate Boc-Lys(trifluoracetyl)-AMC. After an incubation of 60 minutes the reaction was stopped by addition of 20 µM SAHA and the deacetylated substrate was converted into a fluorescent product by the addition of trypsin.

The following results are shown in FIG. 3.

Inhibition of HDACs 1, 5, 7 and 8 by P2742, KA089, KA090 and KA091 was tested. The HDAC activity was investigated using a colorimetric assay as described by Wegener et al. (2003) using 50 µM of the substrate Boc-Lys(Ac)-AMC for HDAC1 or 20 µM of the substrate Boc-Lys(TFA)-AMC for HDAC5, 7 and 8.

The IC$_{50}$-values of P2742 were determined to be 3.0 µM for HDAC1, 0.11 µM for HDAC5, 0.24 µM for HDAC7 and 0.012 µM for HDAC8. For KA089 the IC$_{50}$-values were 20 µM for HDAC1, 13 µM for HDAC5, 0.51 µM for HDAC7 and 0.20 µM for HDAC8. The compound KA090 showed IC$_{50}$-values of 34 µM for HDAC1, 12 µM for HDAC5, 2.1 µM for HDAC7 and 0.071 µM for HDAC8. The IC$_{50}$-values of KA091 were 7.9 µM for HDAC1, 1.0 µM for HDAC5, 0.080 M for HDAC7 and 0.0055 µM for HDAC8.

TABLE 1

IC$_{50}$-values of compounds of the invention on different HDAC isoforms in μM.

IC$_{50}$ (μM)

| Cp | HDAC1 | HDAC2 | HDAC3 | HDAC4 | HDAC5 | HDAC6 | HDAC7 | HDAC8 |
|---|---|---|---|---|---|---|---|---|
| 13a | 3.6 ± 0.8 | 32 ± 1.5 | >50 | 8.6 ± 1.5 | 0.11 ± 0.01 | 6.7 ± 0.8 | 0.22 ± 0.02 | 0.011 ± 0.001 |
| 13b | >50 | >50 | >50 | >50 | >50 | >50 | 1.3 ± 0.7 | 4.4 ± 0.8 |
| 13c | 21 ± 1 | >50 | >50 | >50 | 13 ± 1 | 32 ± 18 | 0.5 ± 0.2 | 0.18 ± 0.02 |
| 13d | 34 ± 2 | >50 | >50 | >50 | 12 ± 1 | 14 ± 1 | 2.0 ± 0.5 | 0.072 ± 0.003 |
| 13e | 7.9 ± 0.2 | >50 | 20 ± 1 | 5.7 ± 0.3 | 1.0 ± 0.1 | 1.2 ± 0.4 | 0.08 ± 0.02 | 0.0059 ± 0.0003 |
| 13f | 2.9 ± 0.3 | >50 | 10 ± 0.56 | 2.84 ± 0.13 | 0.17 ± 0.02 | 9.0 ± 4.0 | 2.6 ± 0.4 | 0.0041 ± 0.0002 |
| 13g | 1.7 ± 0.2 | >50 | 6.7 ± 0.4 | 2.0 ± 0.1 | 0.14 ± 0.02 | 2.8 ± 0.7 | 1.7 ± 0.2 | 0.0029 ± 0.0001 |
| 13h | 35 ± 3 | >50 | >50 | 5.1 ± 0.6 | 0.74 ± 0.16 | 5.2 ± 1.1 | 5 ± 1 | 0.017 ± 0.001 |
| 13i | >50 | >50 | >50 | >50 | >50 | >50 | >50 | 9.2 ± 0.3 |
| 13j | 2.6 ± 0.3 | 16 ± 2 | 7.0 ± 0.5 | 2.3 ± 0.3 | 0.038 ± 0.001 | 1.4 ± 0.2 | 2.0 ± 0.7 | 0.0063 ± 0.0004 |
| 13k | 5.8 ± 0.3 | >50 | 26 ± 4 | 7.6 ± 0.8 | 0.24 ± 0.01 | 1.3 ± 0.3 | 2.5 ± 0.1 | 0.0054 ± 0.0004 |
| 13l | 2.1 ± 0.2 | 30 ± 2 | 5.3 ± 0.4 | 2.2 ± 0.3 | 0.046 ± 0.003 | 0.65 ± 0.11 | 1.5 ± 0.4 | 0.0060 ± 0.0006 |
| 13 | 3.7 ± 0.4 | >50 | 9.6 ± 0.7 | 3.2 ± 0.5 | 0.038 ± 0.002 | 1.3 ± 0.3 | 1.3 ± 0.2 | 0.0043 ± 0.0005 |
| 12a | >50 | >50 | >50 | >50 | >50 | >50 | >50 | 2.8 ± 0.3 |
| 12g | >50 | >50 | >50 | >50 | >50 | >50 | >50 | 0.6 ± 0.1 |
| 12h | >50 | >50 | >50 | >50 | >50 | >50 | >50 | 13 ± 1 |
| 12k | >50 | >50 | >50 | >50 | 33 ± 2 | >50 | >50 | 0.72 + 0.08 |
| 1 | 0.062 ± 0.004 | 0.17 ± 0.01 | 0.054 ± | 27 ± 4 | 24 ± 3 | 0.089 ± 0.007 | 12 ± 1 | 5.3 ± 1.2 |
| 6 | 3.0 ± 0.2 | 45 ± 13 | 38 ± 3 | 10 ± 1 | >50 | 18 ± 6 | 9.8 ± 1.4 | 0.024 + 0.002 |

1 = SAHA;
6 = PCI-34051;
The IC$_{50}$-values were determined using a colorimetric assay as described above.
Controls are SAHA (Vorinostat) and the best known selective HDAC8 inhibitor PCI-34051.

TABLE 2

GI$_{50}$-values of compounds of the invention on different cell lines in μM. The growth inhibition of the cancer cell lines was determined using the resazurin assay.

GI$_{50}$ (μM)

| Cpd | SK-UT-1 | MCF7 | JURKAT |
|---|---|---|---|
| 13a | 736 ± 659 | >1000 | 63 ± 8 |
| 13b | 343 ± 191 | 213 ± 50 | 558 ± 342 |
| 13c | 64 ± 7 | 60 ± 6 | 67 ± 8 |
| 13d | 106 ± 21 | 200 ± 58 | 153 ± 28 |
| 13e | >1000 | >1000 | 56 ± 9 |
| 13f | 147 ± 73 | >1000 | 33 ± 3 |
| 13g | 76 ± 7 | >1000 | 30 ± 3 |
| 13h | >1000 | >1000 | 42 ± 3 |
| 13i | 109 ± 29 | 16 ± 3 | 24 ± 3 |
| 13j | 16 ± 3 | 11 ± 3 | 17 ± 3 |
| 13k | 45 ± 16 | 44 ± 12 | 36 ± 4 |
| 13l | 24 ± 5 | 79 ± 11 | 16 ± 2 |
| 13m | 35 ± 2 | 179 ± 66 | 23 ± 2 |
| 1 (SAHA) | 5.4 ± 0.4 | 3.7 ± 0.4 | 3.7 ± 0.4 |
| 6 (PCI-34051) | 136 ± 62 | 65 ± 18 | 40 ± 4 |

Example 5 Testing of Further Compounds

The conditions were as described in Examples 3 and 4.

TABLE 3

IC$_{50}$-values of further compounds of the invention on HDAC1-8 in μM.

| Cmp | LabIdNr | HDAC1 | HDAC2 | HDAC3 | HDAC4 | HDAC5 | HDAC6 | HDAC7 | HDAC8 |
|---|---|---|---|---|---|---|---|---|---|
| 12a | bh1-104 | >50 | >50 | >50 | >50 | >50 | 4.7 ± 0.6 | >50 | 2.8 ± 0.3 |
| 12b | KA027 | >50 | >50 | >50 | 19 | >50 | >50 | >50 | 16 ± 1 |
| 12c | KA032 | >50 | >50 | >50 | >50 | >50 | >50 | >50 | 23 ± 1 |
| 12d | KA044 | >50 | >50 | >50 | >50 | >50 | 4.7 ± 1 | >50 | 3.8 ± 0.4 |
| 12e | KA028 | — | — | — | — | — | — | — | 0.21 ± 0.01 |
| 12f | NaF09 | >50 | >50 | >50 | >50 | >50 | >50 | >50 | 1.6 ± 0.1 |
| 12g | KA167 | >50 | >50 | >50 | >50 | >50 | 12 ± 2 | >50 | 0.60 ± 0.05 |
| 12h | KA170 | >50 | >50 | >50 | >50 | >50 | >50 | >50 | 12 ± 1 |
| 12i | KA172 | >50 | >50 | >50 | >50 | >50 | >50 | >50 | 2.2 ± 0.2 |
| 12j | NaF11 | >50 | >50 | >50 | >50 | >50 | >50 | >50 | 1.5 ± 0.2 |
| 12k | KA181 | >50 | >50 | >50 | >50 | 33 | >50 | >50 | 0.72 ± 0.08 |
| 12l | NaF12 | >50 | >50 | >50 | >50 | >50 | >50 | >50 | 1.7 ± 0.1 |
| 12m | SaH05 | >50 | >50 | >50 | >50 | 39 | >50 | 15 ± 5 | 1.3 ± 0.1 |
| 12n | KA100 | >50 | >50 | >50 | >50 | >50 | >50 | >50 | 1.2 ± 0.1 |
| 12o | KA092 | >50 | >50 | >50 | >50 | >50 | >50 | >50 | 17 ± 1 |
| 12p | NaF03 | >50 | >50 | >50 | >50 | >50 | >50 | >50 | 1.6 ± 0.3 |
| 12q | NaF15 | >50 | >50 | >50 | >50 | >50 | >50 | >50 | 3.8 ± 0.6 |
| 12r | KA180 | >50 | >50 | >50 | >50 | >50 | >50 | >50 | 4.2 ± 0.2 |
| 12s | SaH02 | >50 | >50 | >50 | >50 | 26 ± 1 | >50 | >50 | 1.9 ± 0.1 |
| 12t | SaH03 | >50 | >50 | >50 | 17 ± 2 | 4.0 ± 0.2 | >50 | 4.5 ± 2 | 0.015 ± 0.002 |

TABLE 3-continued

IC$_{50}$-values of further compounds of the invention on HDAC1-8 in μM.

| Cmp | LabIdNr | HDAC1 | HDAC2 | HDAC3 | HDAC4 | HDAC5 | HDAC6 | HDAC7 | HDAC8 |
|---|---|---|---|---|---|---|---|---|---|
| 12u | SaH04 | >50 | >50 | >50 | >50 | >50 | >50 | 3.4 ± 1 | 2.3 ± 0.2 |
| 12v | SaH06 | >50 | >50 | >50 | >50 | >50 | >50 | >50 | 5.4 ± 0.5 |
| 12w | KA182 | >50 | >50 | >50 | >50 | >50 | >50 | >50 | 1.7 ± 0.1 |
| 12x | KA192 | >50 | >50 | >50 | >50 | 9.5 ± 10.8 | >50 | >50 | 0.46 ± 0.04 |

TABLE 4

GI$_{50}$-values of the further compounds of the invention on different cell lines in μM.

| Compound | SKUT-1 | MCF-7 | Jurkat |
|---|---|---|---|
| 12h | 107 ± 26 | 99 ± 13 | 712 ± 621 |
| 12x | 67 ± 20 | 51 ± 8 | 7.2 ± 0.4 |

Example 6

Cheminformatics

The chemical structures of the imine series were represented by 249 chemical 2D descriptors implemented in the MOE program (Chemical Computing Group Inc.). Subsequently, the relationship between the IC$_{50}$ values against HDAC8 and the chemical structures was analyzed by a classical Principal Component Analysis (PCA) using the same program.

Figure 5:
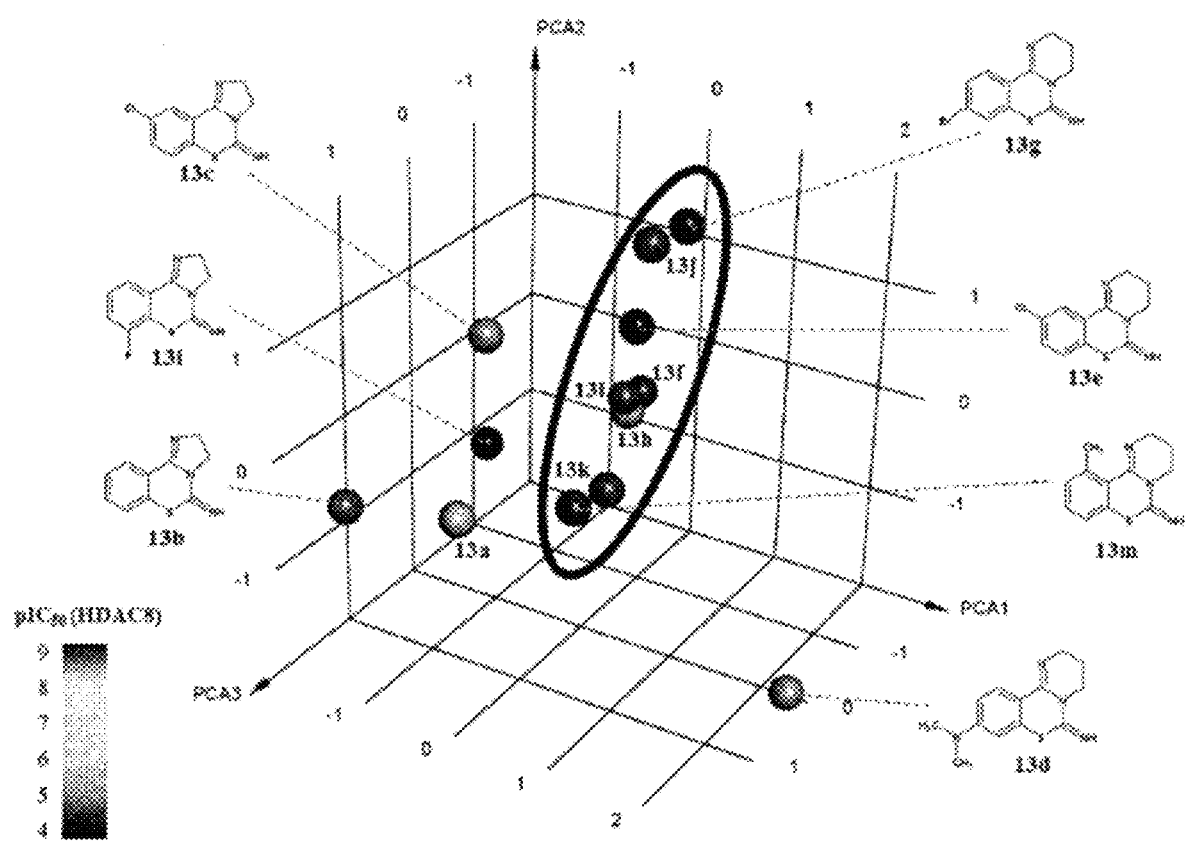
FIG. 5—PCA-Analysis of chemical descriptors characterising compounds of the benzothiazinimine series. Each sphere represents one chemical entity labeled by its code number.

The imine function is crucial for very strong inhibition of HDAC8, because the corresponding thione intermediates 12a-m are substantially less potent against this enzyme (see Table 1). Furthermore, the ring size of the nitrogen heterocycle had a tremendous impact on potency: As demonstrated by the direct comparison of three matching pairs of imine compounds (13a/13b, 13e/13c, 13 h/13i), the 3,4-dihydrobenzo[e]pyrimido[1,2-c][1,3]thiazin-6(2H)-imines were at least 30 times more potent than the corresponding 2H-benzo[e]imidazo[1,2-c][1,3]thiazin-5(3H)-imines. Substitutions with halogens or methyl were well tolerated at each aromatic position of lead compound 13a and lead to IC$_{50}$ values in the single digit nanomolar range. However, a dimethylamino group at R2-position is clearly disfavored and causes a strong drop in activity against the target enzyme. A principal component analysis (PCA) using 2D chemical descriptors of the thiazin-imines is shown in FIG. 5. The most potent compounds with single nanomolar activity are grouped in a prolate cluster which is highlighted by a black ellipsis in the center of the diagram. The PCA illustrates the large chemical space which is covered by diverse compounds with nanomolar potencies. This opens many opportunities to explore all aromatic positions of the thiazin-imine pharmacophore and further optimize the potency of this compound class while preserving beneficial physico chemical parameters. Based on the observed correlation between potency and selectivity we also expect an improvement in the selective recognition of HDAC8.

The features disclosed in the foregoing description, in the claims and/or in the accompanying drawings may, both separately and in any combination thereof, be material for realizing the invention in diverse forms thereof.

REFERENCES

Balasubramanian, S., Ramos, J., Luo, W., Sirisawad, M., Verner, E., and Buggy, J. J. (2008) A novel histone deacetylase 8 (HDAC8)-specific inhibitor PCI-34051 induces apoptosis in T-cell lymphomas, Leukemia 22, 1026-1034.

Bieliauskas, A. V., and Pflum, M. K. (2008) Isoform-selective histone deacetylase inhibitors, Chem Soc Rev 37, 1402-1413.

Butler L M et al. Cancer Res. (2000), 60, 5165-70.

Cancer Facts & FIGS. 2009. Atlanta, Ga. 2009.

Chamoun-Emanuelli A M, Bobardt M, Moncla B, Mankowski M K, Ptak R G, Gallay P, Chen Z. (2014) Evaluation of P D 404,182 as an anti-HIV and anti-herpes simplex virus microbicide. Antimicrob Agents Chemother. 58(2):687-97.

Finnin, M. S., Donigian, J. R., Cohen, A., Richon, V. M., Rifkind, R. A., Marks, P. A., Breslow, R., and Pavletich, N. P. (1999) Structures of a histone deacetylase homologue bound to the TSA and SAHA inhibitors, Nature 401, 188-193.

Giannini G et al., Bioorg. Med. Chem. Lett. (2015), 25, 459-61.

Haberland, M., Mokalled, M. H., Montgomery, R. L., and Olson, E. N. (2009) Epigenetic control of skull morphogenesis by histone deacetylase 8, Genes & development 23, 1625-1630.

Kim S. et al., J. Life Science (2000), 10(2), 39-44.

Marks, P., and Xu, W. S. (2009) Histone deacetylase inhibitors: Potential in cancer therapy, Journal of cellular biochemistry 107, 600-608.

Mizuhara T, Oishi S, Ohno H, Shimura K, Matsuoka M, Fujii N. (2012) Concise synthesis and anti-HIV activity of pyrimido[1,2-c][1,3]benzothiazin-6-imines and related tricyclic heterocycles. Org Biomol Chem. 10(33):6792-802. See also WO 2012/153768 A1.

Nakagawa, M., Oda, Y., Eguchi, T., Aishima, S., Yao, T., Hosoi, F., Basaki, Y., Ono, M., Kuwano, M., Tanaka, M., and Tsuneyoshi, M. (2007) Expression profile of class I histone deacetylases in human cancer tissues, Oncol Rep 18, 769-774.

Niegisch, G., Knievel, J., Koch, A., Hader, C., Fischer, U., Albers, P., and Schulz, W. A. (2013) Changes in histone deacetylase (HDAC) expression patterns and activity of HDAC inhibitors in urothelial cancers, Urologic oncology 31, 1770-1779.

Nociari M M, J. Immunol. Meth. (1998) 213, 157-167.

Oehme, I., Deubzer, H. E., Wegener, D., Pickert, D., Linke, J. P., Hero, B., Kopp-Schneider, A., Westermann, F., Ulrich, S. M., von Deimling, A., Fischer, M., and Witt, O. (2009) Histone deacetylase 8 in neuroblastoma tumorigenesis, Clinical cancer research: an official journal of the American Association for Cancer Research 15, 91-99.

Park, S. Y., Jun, J. A., Jeong, K. J., Heo, H. J., Sohn, J. S., Lee, H. Y., Park, C. G., and Kang, J. (2011) Histone deacetylases 1, 6 and 8 are critical for invasion in breast cancer, Oncol Rep 25, 1677-1681.

Schrump, D. S. (2009) Cytotoxicity mediated by histone deacetylase inhibitors in cancer cells: mechanisms and potential clinical implications, *Clinical cancer research: an official journal of the American Association for Cancer Research* 15, 3947-3957.

Stolfa D A, J. Mol. Biol. (2014), 426, 3442-3453.

Wegener, D., Hildmann, C., Riester, D., and Schwienhorst, A. (2003) Improved fluorogenic histone deacetylase assay for high-throughput-screening applications, *Anal Biochem* 321, 202-208.

The invention claimed is:

1. A method for inhibiting an enzyme of the histone deacetylase (HDAC) family wherein said method comprises incubating the enzyme of the HDAC family with a compound of formula III

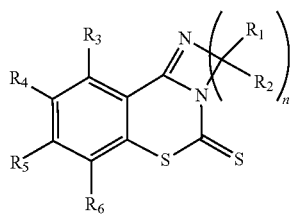

(III)

wherein
n is 2 or 3,
$R_1$ and $R_2$ are hydrogen;
$R_3$, $R_4$, $R_5$, and $R_6$ are each independently selected from
hydrogen,
halogen,
$N(R_{10})_2$,
O—X, $NR_8$—X,
$C_1$-$C_6$ alkyl-X, $C_2$-$C_6$ alkenyl-X, $C_2$-$C_6$ alkynyl-X, $C_1$-$C_6$ heteroalkyl-X, $C_1$-$C_6$ fluoroalkyl-X, $C_1$-$C_6$ alkyl-O—X, $C_1$-$C_3$ alkyl-O—$C_1$-$C_3$ alkyl-X, $C_1$-$C_6$ alkyl-$NR_8$—X, and $C_1$-$C_3$ alkyl-$NR_8$—$C_1$-$C_3$ alkyl-X;
X is hydrogen, $C_1$-$C_6$ alkyl, or $C_2$-$C_6$ alkenyl;
$R_8$ is selected from hydrogen, and $C_1$-$C_6$ alkyl; and
$R_{10}$ is hydrogen, $C_1$-$C_6$ alkyl, or $C_1$-$C_6$ heteroalkyl;
or a pharmaceutically accepted salt thereof.

2. The method of claim 1, wherein the enzyme of the HDAC family is HDAC8.

3. The method of claim 1, wherein
$R_3$, $R_4$, $R_5$ and $R_6$ are each independently selected from hydrogen; halogen; $C_1$-$C_6$ alkyl; $N(R_{10})_2$ with $R_{10}$ being $C_1$-$C_6$ alkyl; and
$C_1$-$C_6$ fluoroalkyl-X with X being hydrogen.

4. The method of claim 1, wherein the compound is selected from:
a compound of formula III wherein $R_3$ is $C_1$-$C_6$ alkyl; and $R_4$, $R_5$, and $R_6$ are each hydrogen;
a compound of formula III wherein $R_3$, $R_4$, and $R_5$ are each hydrogen; and $R_6$ is halogen;
a compound of formula III wherein $R_3$, $R_4$, and $R_6$ are each hydrogen; and $R_5$ is halogen;
a compound of formula III wherein $R_3$, $R_4$, and $R_6$ are each hydrogen; and $R_5$ is $C_1$-$C_6$ alkyl; and
a compound of formula III wherein $R_3$, $R_5$, and $R_6$ are each hydrogen; and $R_4$ is halogen.

5. The method of claim 4, wherein n is 2, $R_3$ is methyl, and $R_4$, $R_5$ and $R_6$ are each hydrogen.

6. The method of claim 4, wherein $R_3$, $R_4$, and $R_5$ are each hydrogen; and $R_6$ is F.

7. The method of claim 4, wherein n is 3; $R_3$, $R_4$, and $R_6$ are each hydrogen; and $R_5$ is Br.

8. The method of claim 4, wherein n is 3; $R_3$, $R_4$, and $R_6$ are each hydrogen; and $R_5$ is methyl.

9. The method of claim 4, wherein n is 2; $R_3$, $R_5$, and $R_6$ are each hydrogen; and $R_4$ is Br.

10. A method for treating cancer, comprising administering to a subject in need of such treatment a therapeutically effective amount of a compound of formula III, or a pharmaceutically accepted salt thereof,

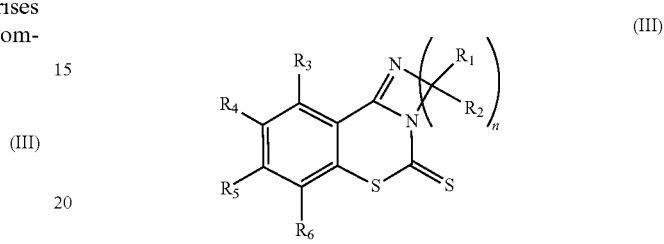

(III)

wherein
n is 2 or 3;
$R_1$ and $R_2$ are hydrogen;
$R_3$, $R_4$, $R_5$, and $R_6$ are each independently selected from
hydrogen,
halogen,
$N(R_{10})_2$,
O—X, $NR_8$—X,
$C_1$-$C_6$ alkyl-X, $C_2$-$C_6$ alkenyl-X, $C_2$-$C_6$ alkynyl-X, $C_1$-$C_6$ heteroalkyl-X, $C_1$-$C_6$ fluoroalkyl-X, $C_1$-$C_6$ alkyl-O—X, $C_1$-$C_3$ alkyl-O—$C_1$-$C_3$ alkyl-X, $C_1$-$C_6$ alkyl-$NR_8$—X, and $C_1$-$C_3$ alkyl-$NR_8$—$C_1$-$C_3$ alkyl-X;
X is hydrogen, $C_1$-$C_6$ alkyl, or $C_2$-$C_6$ alkenyl;
$R_8$ is selected from hydrogen, and $C_1$-$C_6$ alkyl; and
$R_{10}$ is hydrogen, $C_1$-$C_6$ alkyl,
and wherein the cancer is neuroblastoma, a T-cell lymphoma, urothelial cancer or breast cancer.

11. The method of claim 10, wherein the compound is administered in combination with a cytostatic compound.

12. The method of claim 10, wherein
$R_3$, $R_4$, $R_5$ and $R_6$ are each independently selected from hydrogen; halogen; $C_1$-$C_6$ alkyl; $N(R_{10})_2$ with $R_{10}$ being $C_1$-$C_6$ alkyl; and $C_1$-$C_6$ fluoroalkyl-X with X being hydrogen.

13. The method of claim 10, wherein the compound is selected from:
a compound of formula III wherein $R_3$ is $C_1$-$C_6$ alkyl; and $R_4$, $R_5$, and $R_6$ are each hydrogen;
a compound of formula III wherein $R_3$, $R_4$, and $R_5$ are each hydrogen; and $R_6$ is halogen;
a compound of formula III wherein $R_3$, $R_4$, and $R_6$ are each hydrogen; and $R_5$ is halogen;
a compound of formula III wherein $R_3$, $R_4$, and $R_6$ are each hydrogen; and $R_5$ is $C_1$-$C_6$ alkyl; and
a compound of formula III wherein $R_3$, $R_5$, and $R_6$ are each hydrogen; and $R_4$ is halogen.

14. The method of claim 13, wherein n is 2, $R_3$ is methyl, and $R_4$, $R_5$ and $R_6$ are each hydrogen.

15. The method of claim 13, wherein $R_3$, $R_4$, and $R_5$ are each hydrogen; and $R_6$ is F.

16. The method of claim 13, wherein n is 3, $R_3$, $R_4$, and $R_6$ are each hydrogen; and $R_5$ is Br.

17. The method of claim 13, wherein n is 3; $R_3$, $R_4$, and $R_6$ are each hydrogen; and $R_5$ is methyl.

18. The method of claim 1, wherein two or three of $R_3$, $R_4$, $R_5$, and $R_6$ are hydrogen.

19. The method of claim 10, wherein two or three of $R_3$, $R_4$, $R_5$, and $R_6$ are hydrogen.

20. The method of claim 1, wherein $R_3$, $R_4$, $R_5$, and $R_6$ are each hydrogen.

* * * * *

UNITED STATES PATENT AND TRADEMARK OFFICE
CERTIFICATE OF CORRECTION

PATENT NO. : 11,801,251 B2
APPLICATION NO. : 17/141520
DATED : October 31, 2023
INVENTOR(S) : Franz-Josef Meyer-Almes et al.

It is certified that error appears in the above-identified patent and that said Letters Patent is hereby corrected as shown below:

In the Specification

Column 3,
Line 51, "NR—$C_1$-$C_3$ alkyl-X" should read --$NR_8$—$C_1$-$C_3$alkyl-X--

Column 4,
Line 3, "$C_3$-$C_2$cycloalkyl," should read --$C_3$-$C_{10}$cycloalkyl,--

Column 12,
Line 40, "n is 2;" should read --n is 3;--

Column 17,
Line 63, "2N NaOH" should read --2 N $NaOH_{aq}$--

Column 24,
Line 15, "[$M^+$ ($^{79}Br$)]" should read --[$M^+$ ($^{81}Br$)]--

In the Claims

Column 34,
Line 38, "$C_1$-$C_6$ alkyl," should read --$C_1$-$C_6$ alkyl, or $C_1$-$C_6$ heteroalkyl--

Signed and Sealed this
Thirteenth Day of February, 2024

Katherine Kelly Vidal
*Director of the United States Patent and Trademark Office*